(12) United States Patent
Milam et al.

(10) Patent No.: US 8,664,462 B2
(45) Date of Patent: *Mar. 4, 2014

(54) METHOD OF PROCESSING FEED STREAMS CONTAINING HYDROGEN SULFIDE

(71) Applicant: Shell Oil Company, Houston, TX (US)

(72) Inventors: Stanley Nemec Milam, Houston, TX (US); Ann Marie Lauritzen, Houston, TX (US); Michael Anthony Reynolds, Katy, TX (US); Eswarachandra Kumar Paruchuri, Richmond, TX (US); Scott Lee Wellington, Bellaire, TX (US)

(73) Assignee: Shell Oil Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/677,983

(22) Filed: Nov. 15, 2012

(65) Prior Publication Data
US 2013/0123559 A1     May 16, 2013

Related U.S. Application Data

(60) Provisional application No. 61/559,837, filed on Nov. 15, 2011.

(51) Int. Cl.
*C07C 7/00* (2006.01)

(52) U.S. Cl.
USPC ..... 585/802; 48/127.5; 423/573.1; 208/208 R

(58) Field of Classification Search
None
See application file for complete search history.

(56) References Cited

U.S. PATENT DOCUMENTS

| | | |
|---|---|---|
| 4,171,347 A | 10/1979 | Hass |
| 4,563,202 A | 1/1986 | Yao et al. |
| 5,092,121 A | 3/1992 | Ahner et al. |
| 5,520,249 A | 5/1996 | Minkkinen et al. |
| 6,099,819 A | 8/2000 | Srinivas et al. |
| 6,616,908 B2 | 9/2003 | Watson et al. |
| 7,311,891 B2 | 12/2007 | Dolan et al. |
| 7,841,407 B2 | 11/2010 | Wellington et al. |
| 2003/0094366 A1 | 5/2003 | Inaba et al. |
| 2003/0194366 A1 | 10/2003 | Srinivas et al. |
| 2009/0260808 A1 | 10/2009 | Wellington et al. |
| 2011/0185633 A1 | 8/2011 | Betting et al. |

FOREIGN PATENT DOCUMENTS

WO     2011124326     10/2011

*Primary Examiner* — Tam M Nguyen

(57) ABSTRACT

A method of processing feed streams high in hydrogen sulfide is provided. The method includes providing a feed gas stream that includes hydrocarbons and at least 5 vol % hydrogen sulfide. At least a portion of the feed gas stream is separated into a hydrogen sulfide stream and a hydrocarbon stream. The hydrocarbon gas stream is processed to produce natural gas. At least 34 mol. % of the hydrogen sulfide in the hydrogen sulfide stream is combusted with an oxidant to generate thermal power. Thermal power generated by the combustion is utilized in one or more of the steps of separating the feed gas stream into the hydrogen sulfide stream and the hydrocarbon gas stream, and processing the hydrocarbon gas stream to produce natural gas, compressed natural gas, or liquefied natural gas.

20 Claims, 4 Drawing Sheets

METHOD OF PROCESSING FEED STREAMS CONTAINING HYDROGEN SULFIDE

The present application claims the benefit of U.S. Patent Application No. 61/559,837, filed Nov. 15, 2011, the entire disclosure of which is hereby incorporated by reference.

FIELD OF THE INVENTION

The present invention relates to methods for recovery of hydrocarbons from a subsurface hydrocarbon formation. In particular, the present invention relates to methods for processing feed streams containing hydrogen sulfide from subsurface hydrocarbon formations.

BACKGROUND OF THE INVENTION

Hydrocarbons obtained from subsurface formations are often used as energy resources, as feedstocks, and as consumer products. Concerns over depletion of available hydrocarbon resources have led to development of processes for more efficient recovery, processing, and/or use of available hydrocarbon resources.

In conventional processes, fluids obtained from a subsurface hydrocarbon formation may include water and gases and/or liquids. If the fluids obtained from a hydrocarbon subsurface formation contain a mixture of gases and liquids, the gases may be separated from the liquids. In instances where hydrocarbon gases are predominately produced from the subsurface formation, the hydrocarbon gases may be processed to remove impurities and/or inert gases to make fuel (for example, natural gas (pipeline gas), compressed natural gas (CNG), or liquefied natural gas (LNG)). Conventional processing of the subsurface formation gases may include treatment with a regenerative chemical extraction system such as an amine extraction system to capture hydrogen sulfide and/or carbon dioxide from the subsurface formation gases and produce a hydrocarbon gas stream. The hydrocarbon gas stream may be further processed to produce natural gas, CNG, or LNG.

Most commonly, hydrogen sulfide captured from subsurface formation gases is converted to elemental sulfur using a Claus process. The Claus process may be represented by the following equation: $2H_2S+O_2 \rightarrow 2S+2H_2O$. Using the Claus process to treat hydrogen sulfide captured from subsurface formation gases that contain a significant amount of hydrogen sulfide produces a significant amount of elemental sulfur. The potential uses for the generated sulfur, however, have become limited due to oversupply and/or conversion of hydrogen sulfide to the elemental sulfur may be economically disadvantageous. The Claus process generates some power, however, the amount of power generated may be insufficient to operate the processing systems used to capture hydrogen sulfide from the subsurface formation gases and to produce natural gas, CNG, or LNG from the resulting hydrocarbon gas stream; thus supplemental power is required from other sources. A portion of the natural gas produced by the process and/or another fuel source are commonly used as fuel for generation of the required supplemental power.

Some sources of supplemental power are obtained by combusting a sulfur treatment process tail gas containing small amounts of sulfur compounds. For example, U.S. Pat. No. 5,092,121 to Ahner et al. describes a process for generating electricity by combusting a combustion fuel containing sulfur in a gas turbine. A sulfur treatment process tail gas containing carbon dioxide and sulfur-containing compounds is combusted in combination with a purified fuel gas stream in the combustor of a gas turbine or a supplemental firing unit to combust the sulfur-containing compounds. While more energetically efficient than the Claus process in the production of electrical power, the process is still relatively inefficient, and burning of the fuel may result in emission of carbon dioxide and sulfur dioxide to the environment.

Other methods for treating hydrocarbon gas streams containing hydrogen sulfide and/or carbon dioxide separate the hydrogen sulfide and/or carbon dioxide from the hydrocarbon gas stream and inject the hydrogen sulfide and/or carbon dioxide into a subsurface formation. These methods require power for separation, compression, and pumping of the hydrogen sulfide and carbon dioxide into the subsurface formation. The fuel for generating the power is generally supplied by burning a portion of the natural gas produced from the hydrocarbon gas stream and/or other fuel sources. Burning of the fuel is inefficient and may result in emission of carbon dioxide to the environment.

As outlined above, methods for treating hydrocarbon gas streams that contain hydrogen sulfide are known, however, hydrocarbon gas streams having greater than 2% by volume hydrogen sulfide are not generally chosen for development due to numerous concerns including corrosion, environmental emissions management, energy requirements for processing, and/or large amounts of elemental sulfur produced from associated Claus processes. As such, efficient, cost effective methods for processing streams containing hydrocarbons and significant quantities of hydrogen sulfide and/or combinations of hydrogen sulfide and carbon dioxide are desirable.

SUMMARY OF THE INVENTION

The present invention is directed to a method comprising:

providing a feed gas stream comprising hydrogen sulfide and hydrocarbons, wherein the feed gas stream comprises at least 5% by volume hydrogen sulfide;

separating at least a portion of the feed gas stream into a hydrogen sulfide stream and a hydrocarbon gas stream, the hydrogen sulfide stream containing more hydrogen sulfide, by volume percent, than the feed gas stream, and the hydrocarbon gas stream containing less hydrogen sulfide, by volume percent, than the feed gas stream; and processing the hydrocarbon gas stream to produce natural gas; and combusting at least 34 mol % the hydrogen sulfide in the hydrogen sulfide stream with an oxidant containing molecular oxygen to generate thermal power, where the molar ratio of molecular oxygen to hydrogen sulfide in the hydrogen sulfide stream and oxidant that are combusted is at least 1.4:1; and utilizing the thermal power in one or more of the steps of separating the feed gas stream into the hydrogen sulfide stream and the hydrocarbon gas stream, and processing the hydrocarbon gas stream to produce natural gas.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
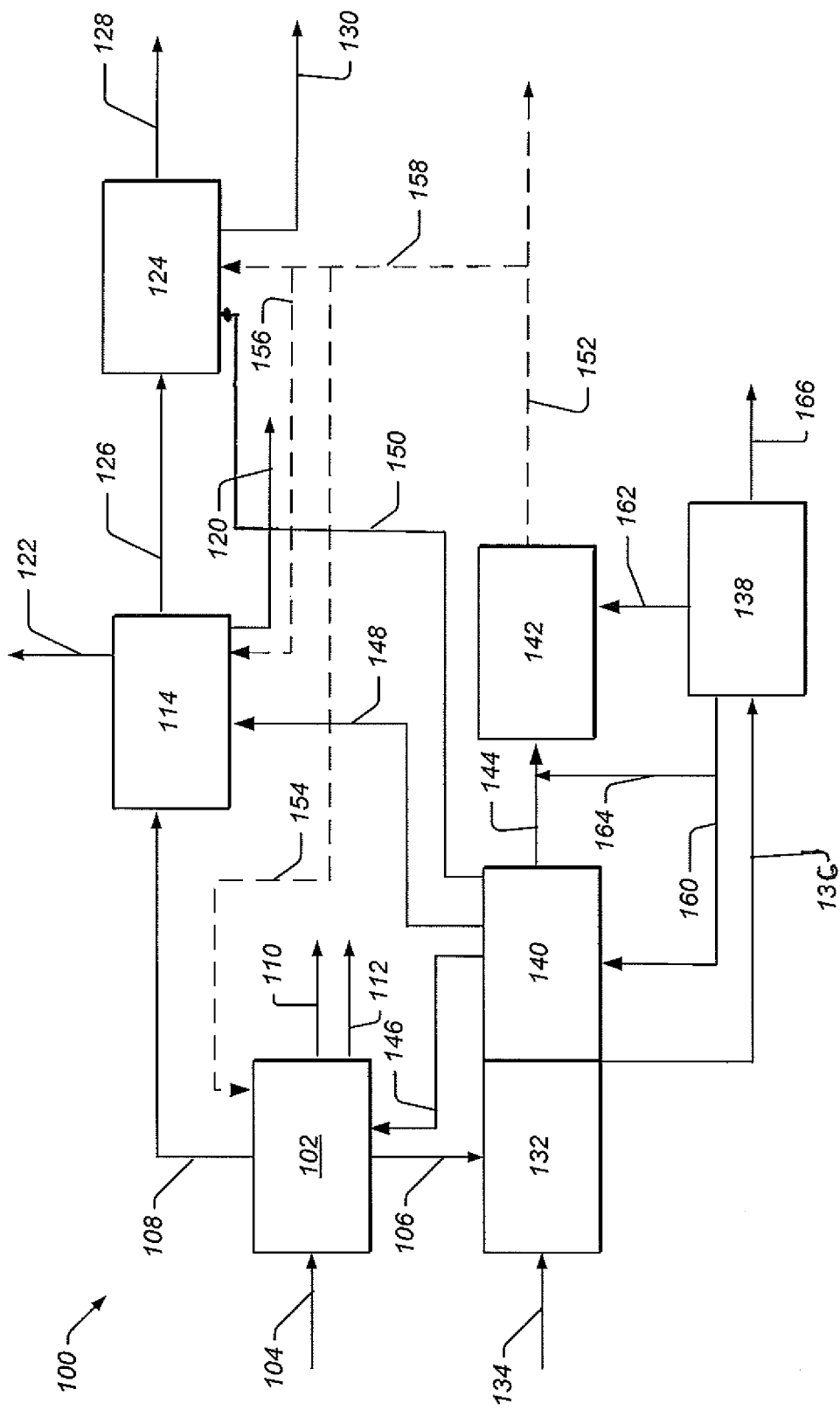
FIG. 1 depicts a schematic of an embodiment of a system for treating a feed gas stream containing significant quantities of hydrogen sulfide to produce power and a natural gas product.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the scope of the invention is defined by the appended claims.

DETAILED DESCRIPTION

The present invention provides a method for utilization of gas streams produced from a subsurface formation that comprises hydrogen sulfide and hydrocarbons. Such gas streams are referred to herein as "feed gas streams." Initially, a feed gas stream is recovered from a subsurface formation. The feed gas stream may be recovered from a subsurface geological formation in accordance with conventional methods for recovering natural gas from subsurface formations.

In the process of the present invention, the feed gas stream is separated into a hydrocarbon gas stream and a hydrogen sulfide stream, where the hydrocarbon gas stream contains less hydrogen sulfide, by volume percent, and the hydrogen sulfide stream contains more hydrogen sulfide, by volume percent, than the feed gas stream. The hydrocarbon gas stream is processed to produce natural gas as either a pipeline natural gas, a compressed natural gas, or a liquefied natural gas product. The hydrogen sulfide stream, or a portion thereof, is combusted, where thermal power generated by the combustion of the hydrogen sulfide stream is utilized to operate the systems and processes for recovering the feed gas stream from the subsurface geological formation, for separating the feed gas stream into the hydrogen sulfide stream and the hydrocarbon gas stream, and for processing the hydrocarbon gas stream to produce natural gas, compressed natural gas, or liquefied natural gas.

A feed gas stream used in the process of the present invention comprises at least 5% by volume hydrogen sulfide. The invention described herein allows for the processing of feed gas streams from subsurface formations previously deemed not suitable for commercial development. Such feed gas streams contain at least 5%, or may contain at least 10%, or at least 20%, or at least 30%, or at least 50%, or at least 90% by volume hydrogen sulfide with the balance being hydrocarbons, other gases, and entrained liquids and particulates. The feed gas stream also contains hydrocarbons, containing at least 0.1%, or at least 1%, or at least 5%, or at least 10%, or at least 25%, or at least 50%, and at most 95%, or at most 90%, or at most 70%, or at most 50%, or at most 10% by volume hydrocarbons. The feed gas stream may also contain carbon dioxide, containing from 0% or from greater than 0% up to 50%, or up to 40%, or up to 30%, or up to 20%, or up to 10%, or up to 5% by volume carbon dioxide. The feed gas stream may contain at least 5%, or at least 10%, or at least 20%, or at least 30%, or at least 50%, or at least 75%, up to 99.9%, or up to 95%, or up to 90%, or up to 80% hydrogen sulfide, by volume, and from 0% up to 50%, or up to 40%, or up to 30%, or up to 20%, or up to 10%, or up to 5% carbon dioxide by volume, and at least 0.1%, or at least 1%, or at least 5%, or at least 10%, or at least 25%, or at least 50%, and at most 95%, or at most 90%, or at most 70% or at most 50% or at most 10% by volume hydrocarbons, with the balance being a mixture of inert gases, including nitrogen and helium, and entrained liquids and particulates. In some embodiments, at least 60%, or at least 70%, or at least 90% of the total volume of hydrogen sulfide and carbon dioxide in the feed gas stream may be hydrogen sulfide, and at most 40%, or at most 30%, or at most 20%, or at most 10% of the total volume of hydrogen sulfide and carbon dioxide in the feed gas stream may be carbon dioxide.

The feed gas stream may also contain organosulfur compounds. Examples of organosulfur compounds include, but are not limited to, mercaptans, sulfides, carbon disulfide, carbonyl sulfide, or mixtures thereof. Examples of mercaptans include, but are not limited to, methanethiol and benzene thiol. Examples of sulfides include, but are not limited to, diethyl sulfide, cyclic sulfides, tetrahydrothiophene, and thiophene compounds.

The feed gas stream recovered from a subsurface formation typically has a wellhead pressure significantly above atmospheric pressure, e.g. at least 3.4 MPa (500 psi), or at least 6.9 MPa (1000 psi), or at least 10.3 MPa (1500 psi). The pressure of the feed gas stream as it flows through the process may be reduced relative to the wellhead pressure, but still may be significantly above atmospheric pressure, e.g., the pressure of the feed gas stream as it flows through the process of the invention is preferably at least 1.7 MPa (250 psi), and more preferably is at least 3.4 MPa (500 psi).

After recovery of the feed gas stream from a subsurface formation, the feed gas stream is then separated into a hydrocarbon gas stream and a hydrogen sulfide stream, where the hydrogen sulfide stream contains more hydrogen sulfide, by volume percent, than the feed gas stream, and the hydrocarbon gas stream contains more hydrocarbons and less hydrogen sulfide, by volume percent, than the feed gas stream. The hydrogen sulfide stream contains at least 1 vol. % more hydrogen sulfide than the feed gas stream, and may contain at least 5 vol. %, or at least 10 vol. %, or at least 25 vol. %, or at least 50 vol. % or at least 75 vol. %, or at least 90 vol. % more hydrogen sulfide than the feed gas stream. The hydrocarbon gas stream contains at least 1 vol. % less hydrogen sulfide than the feed gas stream, and may contain at least 5 vol. %, or at least 10 vol. %, or at least 25 vol. %, or at least 50 vol. %, or at least 75 vol. %, or at least 90 vol. % less hydrogen sulfide than the feed gas stream. The hydrocarbon gas stream contains more hydrocarbons on a volume percentage basis than the feed gas stream, and may contain at least 1 vol. %, or at least 5 vol. %, or at least 10 vol. %, or at least 25 vol. %, or at least 50 vol. %, or at least 75 vol. %, or at least 90 vol. % more hydrocarbons than the feed gas stream.

If the feed gas stream contains carbon dioxide, the carbon dioxide may be separated from the feed gas stream in the hydrogen sulfide stream or may be separated from the feed gas stream as a separate carbon dioxide stream. If the feed gas stream contains carbon dioxide, separation of the carbon dioxide from the feed gas stream may produce a hydrocarbon gas stream containing less carbon dioxide, on a volume percentage basis, than the feed gas stream. For example, the hydrocarbon gas stream may contain at least 1 vol. %, or at least 25 vol. %, or at least 50 vol. %, or at least 75 vol. %, or at least 90 vol. % less carbon dioxide than the feed gas stream.

If the carbon dioxide is separated from the feed gas stream into the hydrogen sulfide stream then the hydrogen sulfide stream may contain more carbon dioxide, on a volume percentage basis, than the feed gas stream. For example, the hydrogen sulfide stream may contain at least 1 vol. %, or at least 25 vol. %, or at least 75 vol. %, or at least 90 vol. % more carbon dioxide than the feed gas stream. Alternatively, if the feed gas stream contains carbon dioxide and the carbon dioxide is separated from the feed gas stream as a separate carbon dioxide stream, both the hydrocarbon gas stream and the hydrogen sulfide stream may have less carbon dioxide, on a volume percentage basis, than the feed gas stream, e.g. both the hydrocarbon gas stream and the hydrogen sulfide stream may contain at least 1 vol. %, or at least 25 vol. %, or at least 50 vol. %, or at least 75 vol. %, or at least 90 vol. % less carbon dioxide than the feed gas stream.

The feed gas stream may be separated into the hydrocarbon gas stream and the hydrogen sulfide stream by physical separation means, e.g. a heat exchanger, a fixed bed adsorption unit, or a pressure swing adsorption unit, or by chemical separation means, e.g. a chemical absorption unit. In a preferred embodiment of the process of the present invention, the feed gas stream is separated into the hydrogen sulfide stream and the hydrocarbon gas stream by contacting and scrubbing the feed gas stream with an amine solvent that removes hydrogen sulfide, and optionally carbon dioxide, from the feed gas stream by absorbing or chemically reacting with the hydrogen sulfide, and optionally with the carbon dioxide. Preferably the hydrogen sulfide, and optionally the carbon dioxide, is reversibly absorbed or reversibly reacted with the amine solvent so that the hydrogen sulfide and carbon dioxide may regenerated apart from the feed gas stream by heating the amine solvent to release the hydrogen sulfide and carbon dioxide together to form the hydrogen sulfide stream and to regenerate the amine solvent or separately to form the hydrogen sulfide stream and a carbon dioxide stream and to regenerate the amine solvent.

When the feed gas stream contains a substantial quantity of carbon dioxide, for example at least 2 vol. % carbon dioxide, the carbon dioxide may be separated from the feed gas stream along with hydrogen sulfide, and may be separated from the hydrogen sulfide prior to combustion of the hydrogen sulfide stream. In an embodiment, the carbon dioxide may be separated from the hydrogen sulfide by temperature differential separation and/or pressure differential separation after the carbon dioxide and the hydrogen sulfide have been separated together from feed gas stream. For example, carbon dioxide and hydrogen sulfide may be separated from the feed gas stream by scrubbing the feed gas stream with an amine solvent, and carbon dioxide may be separated from the amine solvent separately from the hydrogen sulfide by treating the amine solvent containing the carbon dioxide and hydrogen sulfide at a temperature and pressure at which carbon dioxide, but not hydrogen sulfide, is released from the amine solvent. The amine solvent may then be treated in a second step at a second temperature and pressure at which hydrogen sulfide is released from the solvent to form the hydrogen sulfide stream. Alternatively, the carbon dioxide and the hydrogen sulfide may be separated together from the feed gas stream in the hydrogen sulfide stream and the carbon dioxide may be retained in the hydrogen sulfide stream when the hydrogen sulfide in the hydrogen sulfide stream is combusted.

At least a portion of the hydrocarbon gas stream separated from the feed gas stream is processed to produce natural gas, compressed natural gas, and/or liquefied natural gas ("LNG"). Preferably all (100% by volume) of the hydrocarbon gas stream is processed to produce natural gas, compressed natural gas, or LNG, however, a portion of the hydrocarbon gas stream may be utilized for other purposes so that only a portion of the hydrocarbon gas stream is processed to produce natural gas, compressed natural gas, or LNG. Preferably at least 25%, or at least 50%, or at least 75%, or at least 80%, or at least 90%, or at least 95%, by volume, of the hydrocarbon gas stream may be processed to produce natural gas, compressed natural gas, or LNG. At least 90%, or at least 95%, or at least 99% of the produced natural gas, compressed natural gas, or liquefied natural gas may be transported to one or more facilities for storage, further processing, and/or distribution.

As used herein "natural gas" refers to a mixture of hydrocarbons having a carbon number ranging from 1 to 6 ("$C_1$-$C_6$ hydrocarbons") containing more $C_1$ hydrocarbons (methane) than the total amount of $C_2$-$C_6$ hydrocarbons. Hydrocarbons having a carbon number from 1 to 6 include, but are not limited to, methane, ethane, propane, butanes, pentanes, and hexanes. Natural gas, as used herein, may comprise above 50%, or at least 70%, or at least 90%, or at least 95% by volume methane. Natural gas, as used herein, includes "pipeline gas" which is natural gas having a pressure sufficient for transport in natural gas pipelines. Natural gas may have sufficient pressure for transport in natural gas pipelines due to the pressure of the feed gas stream recovered from a subsurface reservoir, or may be compressed to a pressure sufficient for transport in natural gas pipelines, typically from 3.4 MPa (500 psi) for non-trunk natural gas pipelines up to 12.1 MPa (1750 psi) for trunk natural gas pipelines. As used herein, "compressed natural gas" refers to natural gas that has been compressed to less than 1% of its volume (at standard atmospheric pressure), and has a pressure of 13.8 MPa to 27.6 MPa (2000-4000 psi). As used herein "LNG" refers to a liquefied natural gas containing at least 90% methane, preferably at least 95% methane, and more preferably at least 99% methane.

As used herein, "processing the hydrocarbon gas stream to produce natural gas" includes one or more of the steps of 1) dehydrating the hydrocarbon gas stream; 2) removing metals from the hydrocarbon gas stream; 3) separating non-hydrocarbon gases (e.g. nitrogen, helium, carbon oxides, and trace hydrogen sulfide) from the hydrocarbon gas stream; and 4) condensing heavier hydrocarbons from the hydrocarbon gas stream. A further step of compressing the natural gas to a pressure sufficient for distribution in a pipeline ("pipeline gas"), typically from 3.4 MPa (500 psi) to 12.1 MPa (1750 psi), may also be included in the definition of the process of producing a natural gas from the hydrocarbon gas stream if the natural gas produced by the process has a pressure less than required for the pipeline through which the natural gas is to be distributed. Compressed natural gas may be formed from the natural gas by processing the natural gas with at least the additional step of 5) compressing the natural gas to a pressure of from 13.8 MPa to 27.6 MPa (2000-4000 psi). As used herein, the term "processing the hydrocarbon gas stream to produce compressed natural gas" includes the steps of processing the hydrocarbon gas stream to produce natural gas with at least the additional step of compressing the natural gas to a pressure of from 13.8 MPa to 27.6 MPa. Liquefied natural gas (LNG) may be formed from the natural gas by processing the natural gas with the additional steps of 5) optionally, compressing the natural gas to a pressure of at least 5.5 MPa (800 psi), or at least 6.9 MPa (1000 psi) if the natural gas has a pressure of less than 5.5 MPa; 6) optionally, separating at least a portion of hydrocarbons having a carbon number of from 2 to 6 ($C_2$-$C_6$) from the natural gas having a pressure of at least 5.5 MPa to form a methane-rich gas; and 7) liquefying the methane-rich gas or the natural gas having a pressure of at least 5.5 MPa. The term "processing the hydrocarbon gas stream to produce liquefied natural gas (LNG)" includes the steps of processing the hydrocarbon gas stream to produce a natural gas with at least the additional steps of: optionally compressing the natural gas to a pressure of at least 5.5 MPa; optionally separating at least a portion of hydrocarbons having a carbon number of from 2 to 6 ($C_2$-$C_6$) from the natural gas having a pressure of at least 5.5 MPa to form a methane-rich gas; and liquefying the methane-rich gas or the natural gas having a pressure of at least 5.5 MPa. In an embodiment, processing the hydrocarbon gas stream to produce LNG includes the steps of 1) dehydrating the hydrocarbon gas stream; 2) removing metals from the hydrocarbon gas stream; 3) separating non-hydrocarbon gases (e.g. nitrogen, helium, carbon oxides, and trace hydrogen sulfide) from the hydrocarbon gas stream to produce a natural gas; 4) compressing the natural gas to a pressure of at least 5.5 MPa; 5) separating at least a portion of hydrocarbons having a carbon number of from 2 to 6 ($C_2$-$C_6$ hydrocarbons) from the compressed natural gas to produce a methane-rich gas; and 6) liquefying the methane-rich gas. In an embodiment, processing the hydrocarbon gas stream to produce LNG includes steps 1-6 as described in the immediately preceding sentence with the additional step of separating at least a portion of the hydrocarbons having a carbon number of from 2 to 6 from the hydrocarbon gas stream.

The processes and systems for recovering the feed gas stream from a subsurface formation, separating the feed gas stream into the hydrocarbon gas stream and the hydrogen sulfide stream, and for further processing of the hydrocarbon gas stream to form natural gas (pipeline gas), compressed natural gas, or LNG require power. The present invention provides a method in which a hydrogen sulfide stream, or a portion thereof, derived from a feed gas stream is combusted to generate thermal power, where the thermal power generated by combustion of the hydrogen sulfide stream is utilized to effect recovery of the feed gas stream from a subsurface geological formation; separation of the feed gas stream into the hydrogen sulfide stream and the hydrocarbon gas stream; and further processing of the hydrocarbon gas stream to form natural gas (pipeline gas), compressed natural gas, or LNG. The thermal power may also be utilized to effect the separation of carbon dioxide, if any, from the feed gas stream or from a combustion stream and/or to liquefy such carbon dioxide. Combustion of the hydrogen sulfide stream generates sufficient thermal power to effect each step of the process of the invention.

The power required for recovering the feed gas stream from a subsurface geological formation; separating the feed gas stream into the hydrogen sulfide stream and a hydrocarbon gas stream; for processing the hydrocarbon gas stream into natural gas, compressed natural gas, or LNG; for separating carbon dioxide from the feed gas stream or a combustion stream; and for liquefying carbon dioxide may include thermal power, mechanical power, electrical power, or combinations thereof. The thermal power produced by combustion of the hydrogen sulfide stream may be converted to mechanical power, electrical power, or the appropriate type of thermal power, as needed, to effect: recovering the feed gas stream from a subsurface geological formation; separating the feed gas stream into the hydrogen sulfide stream and a hydrocarbon gas stream; processing the hydrocarbon gas stream into natural gas, compressed natural gas, or LNG; separating carbon dioxide, if any, from the feed gas stream or a combustion stream; and liquefying carbon dioxide.

In order to generate the thermal power required to effect recovery of the feed gas stream from a subsurface formation; separation of the feed gas stream into a hydrocarbon gas stream and a hydrogen sulfide gas stream; and further processing of the hydrocarbon gas stream to produce natural gas, compressed natural gas or LNG at least a portion of the hydrogen sulfide stream is combusted with an oxidant comprising molecular oxygen. Preferably, at least 34 mol. %, or at least 50 mol. %, or at least 60 mol. %, or at least 75 mol. %, or at least 80 mol. %, or at least 90 mol. %, or at least 95 mol. %, or most preferably all of the hydrogen sulfide in the hydrogen sulfide stream is combusted to provide the thermal power.

The amount of hydrogen sulfide in the feed gas stream necessary for combustion to provide all the power to separate the hydrogen sulfide stream and the hydrocarbon gas stream and to process the hydrocarbon gas stream to natural gas (pipeline gas), compressed natural gas, or liquefied natural gas depends on the natural gas product to be produced due to the differing quantities of power required to produce the different types of natural gas products. For example, a feed gas stream containing at least 5% by volume hydrogen sulfide provides sufficient hydrogen sulfide that may be separated into a hydrogen sulfide stream for combustion to generate sufficient thermal power effective to separate the feed gas stream into a hydrogen sulfide stream and a hydrocarbon gas stream and to process the hydrocarbon gas stream to produce a pipeline natural gas. A feed gas stream containing at least 10% by volume hydrogen sulfide provides sufficient hydrogen sulfide that may be separated into a hydrogen sulfide stream for combustion to generate sufficient thermal power effective to separate the feed gas stream into a hydrogen sulfide stream and a hydrocarbon gas stream and to process the hydrocarbon gas stream to produce a compressed natural gas. A feed gas stream containing at least 20 vol. % hydrogen sulfide provides sufficient hydrogen sulfide that may be separated into a hydrogen sulfide stream for combustion to generate sufficient thermal power effective to separate the feed gas stream into a hydrogen sulfide stream and a hydrocarbon gas stream and to process the hydrocarbon gas stream to produce liquefied natural gas.

The hydrogen sulfide stream is combusted with a stoichiometric equivalent of oxidant, a stoichiometric excess of oxidant, or slightly less than a stoichiometric equivalent of oxidant to generate the thermal power. As used herein, a "stoichiometric equivalent of oxidant" relative to the combusted portion of the hydrogen sulfide stream refers to an amount of oxidant sufficient to oxidize the hydrogen sulfide in the portion of the hydrogen sulfide stream that is combusted to sulfur dioxide and water according to the reaction equation: $2H_2S + 3O_2 \rightarrow 2SO_2 + 2H_2O$, e.g. an amount of oxidant sufficient to provide 1.5 moles of molecular oxygen per 1 mole of hydrogen sulfide in the portion of the hydrogen sulfide stream that is combusted. A stoichiometric excess of oxidant relative to the portion of the hydrogen sulfide stream that is to be combusted is an amount of oxidant sufficient to provide more than 1.5 moles of molecular oxygen per 1 mole of hydrogen sulfide in the portion of the hydrogen sulfide stream that is combusted. Slightly less than a stoichiometric equivalent of oxidant relative to the portion of the hydrogen sulfide stream that is to be combusted, e.g. from 1.4 up to 1.5 moles of molecular oxygen per mole of hydrogen sulfide in the combusted portion of the hydrogen sulfide stream, may be provided for combustion with the hydrogen sulfide stream in order to inhibit further oxidation of sulfur dioxide to sulfur trioxide or sulfuric acid. In the process of the present invention, the hydrogen sulfide stream is combusted with an oxidant such that the molar ratio of molecular oxygen in the oxidant to hydrogen sulfide in the hydrogen sulfide stream is at least 1.4 to 1.

As used herein, "oxidant" refers to a composition comprising molecular oxygen that may be combusted with hydrogen sulfide. Examples of oxidants include oxygen, oxygen admixed with steam, oxygen admixed with carbon dioxide, air, and/or enriched air. "Enriched air" refers to air having an oxygen content greater than about 21 percent by volume. Enriched air may be used to increase, relative to air, the combustion temperature of the hydrogen sulfide stream at a constant fuel input rate and/or to facilitate post combustion processing of the combustion effluent gases.

Combustion of the hydrogen sulfide stream in the presence of a stoichiometric equivalent, a stoichiometric excess, or slightly less than a stoichiometric equivalent of oxidant relative to the molar amount of hydrogen sulfide in the hydrogen sulfide stream produces a combustion stream comprising sulfur dioxide and water. The resulting sulfur dioxide may be converted to commercial products such as, for example, sulfuric acid. In some embodiments, sulfur dioxide produced by the combustion of the hydrogen sulfide stream is used to facilitate recovery of hydrocarbons from a subsurface geological formation. Water resulting from combustion of the hydrogen sulfide stream may be used in other processing units, stored, or transported to other processing facilities.

If the hydrogen sulfide stream contains significant quantities of carbon dioxide or organosulfur hydrocarbons, the combustion stream will contain significant quantities of carbon dioxide. The carbon dioxide and sulfur dioxide may be separated and sold as one or more commercial products. At least a portion of the carbon dioxide and sulfur dioxide products may be sequestered either individually or together in a subsurface geological formation.

Substantially all of the thermal power generated by combustion of the hydrogen sulfide stream or a portion thereof may be captured as steam having a selected temperature and/or pressure profile, e.g. at least 80%, or at least 85%, or at least 90%, up to 95%, or up to 97%, or up to 99%, or up to 100% of the thermal power generated from combustion may be captured as steam. All or substantially all of the thermal power from combustion of the hydrogen sulfide stream may be used to generate steam at pressures ranging from 0.34 MPa to 34.5 MPa, or from 3.4 MPa to 34.5 MPa, or from 13.8 MPa to 34.5 MPa, or from 22.2 MPa to 34.5 MPa; or from 30 MPa to 34.5 MPa; and temperatures ranging from 135° C. to 650° C., or from 240° C. to 650° C., or from 335° C. to 650° C., or from 375° C. to 650° C.

Thermal power captured as steam may be utilized to provide thermal power, and/or utilized to make mechanical power and/or electrical power for the systems and process used in the process of the present invention. At least a portion of the captured steam is utilized to provide or generate all of the power (thermal, mechanical, and/or electrical) required for recovering the feed gas stream from a subsurface geological formation, for separating the feed gas stream into the hydrogen sulfide stream and the hydrocarbon gas stream, and/or for processing the hydrocarbon gas stream to form natural gas, compressed natural gas, or LNG, and, optionally to separate carbon dioxide from the feed gas stream or the combustion stream and to compress or liquefy the separated carbon dioxide.

The steam generated by capturing the thermal power from combusting the hydrogen sulfide stream may be saturated steam, superheated steam, supercritical steam or ultra supercritical steam based on the power requirements of systems selected to recover the feed gas stream from a subsurface geological formation; to separate the feed gas stream into the hydrogen sulfide stream and the hydrocarbon gas stream; and/or to process the hydrocarbon gas stream into natural gas, compressed natural gas, or LNG, as well as the requirements of systems selected to produce energy for export. As used herein, "saturated steam" is defined as steam in equilibrium with liquid water; "superheated steam" is defined as steam at a temperature higher than water's boiling point at a selected pressure; "supercritical steam" is defined as steam having a temperature of at least 374° C. and a pressure of at least 22.15 MPa, and "ultra supercritical steam" is defined as steam having a temperature of at least 374° C. and a pressure of at least 30 MPa.

Selection of the type of steam to be generated may depend on the systems and processes that require mechanical and/or thermal and/or electrical power. For example, low pressure saturated steam may be preferred to provide thermal power to a regenerative chemical unit reboiler used in the chemical separation of the hydrogen sulfide stream and the hydrocarbon gas stream from the feed gas stream. Higher pressure saturated and/or superheated steam may be preferred to produce mechanical power to drive equipment for purification and/or compression of natural gas while very high pressure supercritical and/or ultra supercritical steam may be used for the production of electrical power using a steam turbine. For example, superheated steam, e.g. supercritical steam or ultra supercritical steam, may be converted to mechanical power by expansion through a steam expansion device (for example, a steam turboexpander or a steam turbine). The mechanical power (shaft power) may be used to drive rotating equipment such as gas compressors, pumps and electric generators.

Combustion of at least 34 mol. %, and preferably all, of the hydrogen sulfide in the hydrogen sulfide stream separated from the feed gas stream with a stoichiometric equivalent, or a stoichiometric excess, or slightly less than a stoichiometric equivalent of an oxidant in accordance with the process of the present invention generates substantial power. Combustion of at least 34 mol. %, or at least 50 mol. %, or at least 60 mol. %, or at least 75 mol. %, or at least 80 mol. %, or at least 90 mol. %, or all of the hydrogen sulfide in the hydrogen sulfide stream with a stoichiometric equivalent, stoichiometric excess, or slightly less than a stoichiometric equivalent of an oxidant relative to the molar amount of hydrogen sulfide in the combusted portion of the hydrogen sulfide stream may generate at least 1.6 megawatts of thermal power (hereinafter "$MW_t$"), or at least 2 $MW_t$, or at least 3 $MW_t$, or at least 4 $MW_t$ per metric ton of hydrogen sulfide in the portion of the hydrogen sulfide stream that is combusted. Utilizing a feed gas stream containing at least 5 vol. % hydrogen sulfide, combustion of at least 34 mol. % of the hydrogen sulfide in the hydrogen sulfide stream may generate at least 300 $MW_t$, or at least 400 $MW_t$, or at least 500 $MW_t$, or at least 1000 $MW_t$, or from 0.01 $MW_t$ to 80000 $MW_t$, or from 200 $MW_t$ to 75000 $MW_t$, or from 300 $MW_t$ to 70000 $MW_t$, or from 400 $MW_t$ to 65000 $MW_t$, or from 500 $MW_t$ to 60000 $MW_t$ per 10 million metric tons of natural gas produced from the feed gas stream according to the process of the invention.

The power generated by combustion of the hydrogen sulfide stream may exceed, often substantially, the power required to recover the feed gas stream from a subsurface geological formation; separate the feed gas stream into the hydrogen sulfide stream and the hydrocarbon gas stream; process the hydrocarbon gas stream to produce a natural gas product selected from the group consisting of pipeline natural gas, compressed natural gas, and liquefied natural gas; and, optionally, separate carbon dioxide from the feed gas stream and compress and/or liquefy the carbon dioxide separated from the feed gas stream. Power required to separate the feed gas stream into the hydrocarbon gas stream and the hydrogen sulfide stream is defined herein to include the step of regenerating the hydrogen sulfide stream from a physical or chemical treatment system, e.g. regenerating the hydrogen sulfide stream from an amine absorption solvent, if such regeneration is required to produce the hydrogen sulfide stream.

The amount of excess power generated by combustion of the hydrogen sulfide stream in accordance with the process of the present invention over and above the power needed to conduct the process may be very substantial. At least 10 kW$_t$, or at least 500 kW$_t$, or at least 1 MW$_t$, or at least 1.5 MW$_t$ of excess thermal power per metric ton of hydrogen sulfide combusted may be generated by combustion of the hydrogen sulfide stream in accordance with the process of the present invention. At least 1 kW$_t$ (kilowatts of thermal power), or at least 100 kW$_t$, or at least 1 MW$_t$, or at least 10 MW$_t$, or at least 100 MW$_t$ of thermal power may be generated in excess of the amount of all the power, including mechanical, thermal, and electrical power, required to: recover the feed gas stream from a subsurface geological formation; separate the feed gas stream into the hydrogen sulfide stream and the hydrocarbon gas stream; process the resulting hydrocarbon gas stream to produce 10 million metric tons of a natural gas product selected from the group consisting of natural gas (pipeline gas), compressed natural gas, and LNG; and, optionally, to compress and/or liquefy carbon dioxide separated from the feed gas stream or a combustion stream produced by combustion of the hydrogen sulfide stream. Excess thermal power generated by combustion of the hydrogen sulfide stream in accordance with the process of the present invention may range from at least 0.001 MW$_t$ to 80000 MWt, or from 200 MWt to 75000 MWt or from 300 MWt to 70000 MWt. or from 400 MWt to 65000 MWt, or from 500 MWt to 60000 MWt per 10 million metric tons of natural gas produced from the feed gas stream in accordance with the process of the invention.

The amount of excess power generated by combustion of the hydrogen sulfide stream, if any, is proportional to the amount of hydrogen sulfide in the feed gas stream and is proportional to the quantity of the hydrogen sulfide stream that is combusted. As the hydrogen sulfide content of the feed gas stream increases the volume of the hydrogen sulfide stream that may be separated from the feed gas stream increases. As a result, combustion of the hydrogen sulfide stream generates more power per selected quantity of feed gas stream (and natural gas produced therefrom) relative to combustion of a hydrogen sulfide stream separated from a feed gas stream containing less hydrogen sulfide (and natural gas produced therefrom). Further, as increasing amounts of the hydrogen sulfide stream are combusted, on a volume percentage basis, more power is generated. In a preferred embodiment the entire hydrogen sulfide stream is combusted to maximize the thermal power generated from the combustion.

Thermal power may generated in such excess relative to the power requirements for recovering the feed gas stream from a subsurface geological formation; for separating the hydrogen sulfide stream and the hydrocarbon gas stream from the feed gas stream; for further processing of the hydrocarbon gas stream to produce natural gas, compressed natural gas, or LNG; and optionally for separating carbon dioxide from the feed gas stream or from a combustion stream, and for compressing and/or liquefying the separated carbon dioxide, that the excess thermal power may be converted to electrical power which may be exported, for example, to power distribution grids, industrial electric smelters, and/or server farms. Electrical power may be produced from the thermal power as described in further detail below, typically at a conversion efficiency of from 35%-60%, where the electrical power produced from the excess thermal power may be produced at a ratio of at least 70 MW of electrical power (hereafter "MW$_e$"), or at least 100 MW$_e$, or at least 200 MW$_e$, or at least 300 MW$_e$, or at least 400 MW$_e$, or at least 500 MW$_e$ per 10 million metric tons of natural gas, compressed natural gas, or LNG produced.

In comparison, conventional processes for producing natural gas, compressed natural gas, or LNG from hydrocarbon feed gas streams containing significant amounts of hydrogen sulfide, or hydrogen sulfide and carbon dioxide—wherein elemental sulfur is produced by application of the Claus process to hydrogen sulfide separated from a hydrocarbon feed gas stream—do not provide power comparable to the power produced by the process of the present invention. The Claus process is conducted in two steps, first oxidation of ⅓ of the hydrogen sulfide, on a molar basis, of a hydrogen sulfide stream according to the following equation: $2H_2S+3O_2 \rightarrow 2SO_2+2H_2O$ followed by reaction of the remaining ⅔ of the hydrogen sulfide, on a molar basis, of the hydrogen sulfide stream with the products of the oxidation step according to the following equation: $4H_2S+2SO_2 \rightarrow 6S+4H_2O$, where the overall reaction equation of the two steps is: $2H_2S+O_2 \rightarrow 2S+2H_2O$ (substoichiometric oxidation of the hydrogen sulfide). Excluding latent heat produced by condensation of sulfur produced in the reaction, the reaction energy of the overall Claus process is 1.446 MWh per metric ton of hydrogen sulfide (1.446 MW$_t$ thermal power per metric ton of hydrogen sulfide). Including latent heat produced by condensation of sulfur, the overall energy produced by the Claus process is 1.836 MWh per metric ton of hydrogen sulfide and per metric ton of sulfur condensed (1.836 MW$_t$ thermal power per metric ton of hydrogen sulfide and per metric ton of sulfur condensed). In comparison, complete combustion of a hydrogen sulfide stream with a stoichiometric equivalent or excess of oxidant provides a reaction energy of 4.230 MWh per metric ton of hydrogen sulfide (4.230 MW$_t$ thermal power per metric ton of hydrogen sulfide). Therefore, the process of the present invention may provide from greater than 1.446 MW$_t$ to 4.230 MW$_t$ of thermal power per metric ton of hydrogen sulfide combusted in the hydrogen sulfide stream as a result of combusting greater than one-third to all of the hydrogen sulfide stream with a stoichiometric equivalent, or a stoichiometric excess, or slightly less than a stoichiometric equivalent of an oxidant relative to the molar amount of hydrogen sulfide in the combusted portion of the hydrogen sulfide stream to generate power.

In the process of the present invention, substantially none, or none, of the hydrocarbons separated from the feed gas stream into the hydrocarbon gas stream need be used as fuel to generate power to conduct the process. Combustion of the hydrogen sulfide stream, may provide at least sufficient power to conduct the process of the invention as described herein. For example, in the process of the present invention 0 vol. %, or from greater than 0 vol. % to at most 0.1 vol. %, or at most 0.5 vol. %, or at most 1 vol. %, or at most 2 vol. %, or at most 5 vol. % of the hydrocarbon gas stream separated from the feed gas stream, or a natural gas, compressed natural gas, or LNG produced from the hydrocarbon gas stream or from any other source, is used as fuel to generate power to conduct the process.

As a result, the process of the present invention also provides a method that generates a minimal amount of, or substantially no, carbon dioxide while generating power. Complete combustion of greater than one-third, and preferably all, of the hydrogen sulfide stream on a volume basis to generate power generates at most 0.1 grams of carbon dioxide per gram of hydrocarbons in the feed gas stream, and may generate from greater than 0 grams to at most 0.1 grams, or to at most 0.05 grams, or to at most 0.01 grams of carbon dioxide per gram of hydrocarbons in the feed gas stream. Since the hydrogen sulfide stream is used as fuel instead of the hydrocarbons from the hydrocarbon gas stream and/or hydrocarbons from other sources, production of carbon dioxide is avoided relative to processes that utilize hydrocarbons as fuel. For example, combustion of methane produces carbon dioxide as a by-product, as shown by the following reaction: $CH_4 + 2O_2 \rightarrow CO_2 + 2 H_2O$. In contrast, combustion of hydrogen sulfide generates sulfur dioxide and water, as shown by the following reaction: $H_2S + 1.5O_2 \rightarrow SO_2 + H_2O$.

In comparison, conventional processes for producing natural gas, compressed natural gas, or LNG from hydrocarbon feed gas streams containing significant amounts of hydrogen sulfide, or hydrogen sulfide and carbon dioxide—wherein elemental sulfur is produced by application of the Claus process to hydrogen sulfide separated from a hydrocarbon feed gas stream—typically require combustion of supplemental fuel to meet the overall power requirements of the process. Such supplemental fuel is generally supplied from the natural gas or compressed natural gas produced by the process. Combustion of the natural gas or compressed natural gas as supplemental fuel leads to significant production of carbon dioxide, and utilizes a portion of the natural gas, compressed natural gas, or LNG product of the process to drive the process. Carbon dioxide produced in a conventional process may be emitted into the atmosphere or specific steps that require additional energy and equipment must be taken to capture the produced carbon dioxide.

Use of the hydrogen sulfide stream as fuel in accordance with the process of the present invention instead of a hydrocarbon fuel enables commercially practical recovery of hydrocarbons from sour hydrocarbon-containing gas subsurface formations containing significant quantities of hydrogen sulfide. Conventionally, the amount of power required to separate hydrogen sulfide from a sour hydrocarbon feed gas stream has provided a practical commercial limit on recovery of sour hydrocarbon feed gases from subsurface formations—sour hydrocarbon feed gases requiring more energy to separate hydrogen sulfide from the feed gas than chemical energy contained in the resulting natural gas product are not recovered since more energy is required to conduct the process than is produced by the process. Thus, previously undesirable feed gas streams that contain hydrocarbons and at least 5 vol. % hydrogen sulfide may be produced from subsurface formations and used as a source of commercial products (for example natural gas, compressed natural gas, liquefied natural gas, liquefied carbon dioxide and sulfur dioxide) because the hydrogen sulfide produced from the feed gas stream is used as the primary or only fuel source for generation of all the power required to operate the feed gas treatment system.

FIG. 1 depicts a schematic representation of a system for treatment of a feed gas stream 104 that includes hydrocarbons and at least 5% by volume of hydrogen sulfide to produce natural gas, compressed natural gas, liquefied natural gas, liquefied carbon dioxide if carbon dioxide is present in the feed gas stream, sulfur dioxide, power, or combinations thereof. The feed gas stream may be produced from a subsurface geological formation. In some embodiments, the feed gas stream includes organosulfur compounds. Examples of organosulfur compounds include, but are not limited to, mercaptans, sulfides, carbon disulfide, carbonyl sulfide, or mixtures thereof. Examples of mercaptans include, but are not limited to, methanethiol and benzene thiol. Examples of sulfides include, but are not limited to, diethyl sulfide, cyclic sulfides, tetrahydrothiophene, and thiophene compounds.

The feed gas stream 104 comprises at least 5%, or at least 10%, or at least 20%, or at least 25%, or at least 30% up to 99.9%, or up to 95%, or up to 90%, or up to 80%, or up to 75%, or up to 60% by volume hydrogen sulfide. The volume percent of hydrogen sulfide in the feed gas stream may range from 5 to up to 99.9, from 20 to 90, or from 30 to 80. In some embodiments, the feed gas stream comprises at least 5%, or at least 10%, at least 20%, or at least 50% or at least 60% by volume hydrogen sulfide and at least 2%, or at least 5%, or at least 10% or at least 20% or at least 30% by volume carbon dioxide. The feed gas stream contains at most 95%, or at most 90%, or at most 70% or at most 50% or at most 10% and at least 0.1%, or at least 1%, or at least 5% or at least 10% by volume hydrocarbons. The feed gas stream 104 preferably has a pressure of at least 1.7 MPa (250 psig), and more preferably has a pressure of at least 3.4 MPa (500 psig) or at least 6.9 MPa (1000 psig), where the pressure of the feed gas stream is derived from the pressure of the subsurface formation from which the feed gas stream is provided.

In system 100 of FIG. 1, the feed gas stream 104 enters feed gas separation unit 102. In feed gas separation unit 102, the feed gas stream 104 is separated into a hydrogen sulfide stream 106, a hydrocarbon gas stream 108, a water stream 110 and/or a stream of hydrocarbons 112 that are condensable at 25° C. and 0.101 MPa (hereinafter "liquid hydrocarbons"). In an embodiment, when carbon dioxide is present, the hydrogen sulfide stream 106 separated from the feed gas stream 102 may also contain carbon dioxide. Optionally, when the feed gas stream contains at least 2 vol. % carbon dioxide, the feed gas stream may be separated into a hydrogen sulfide stream 106, a hydrocarbon gas stream 108, and a carbon dioxide stream (not shown) by separating hydrogen sulfide and carbon dioxide from the feed gas stream and separating the hydrogen sulfide and carbon dioxide into a hydrogen sulfide stream 106 and a carbon dioxide stream, respectively. The hydrogen sulfide stream 106, optionally containing carbon dioxide, contains more hydrogen sulfide, and, optionally more carbon dioxide, by volume percent, than the feed gas stream 104, and the hydrocarbon gas stream 108 contains more hydrocarbons and less hydrogen sulfide, and, optionally less carbon dioxide, by volume percent, than the feed gas stream 104.

Feed gas separation unit 102 may include one or more physical treatment systems and/or one or more chemical treatment systems. A physical treatment system may be, but is not limited to, a coalescing unit, a cyclone separator unit, an electrostatic precipitator unit, a fixed bed adsorption unit, a filter, a heat exchanger, a membrane unit, a pressure swing adsorption unit, and/or a temperature separation unit. The hydrogen sulfide stream 106 and the hydrocarbon gas stream 108 may be separated from the feed gas stream 104 using one or more physical treatment systems in the feed gas separation unit 102. In an embodiment, at least a portion of the water 110 and the condensable hydrocarbons 112 are separated from the feed gas stream 104 by cooling the feed gas stream to a temperature below the dewpoint of water and/or the condensable hydrocarbons in a heat exchanger or a temperature separation unit in the feed gas separation unit 102.

A chemical treatment system in the feed gas separation unit 102 may be an absorption unit. The chemical treatment system may be regenerative such that the chemical treatment system may absorb or react with target components in the feed gas stream such as hydrogen sulfide and carbon dioxide to remove the target components from the feed gas stream and the target components may subsequently be released from the chemical treatment system after separation from the feed gas stream, for example, by the application of thermal power (heat) to the chemical treatment system. Compositions used in a chemical treatment unit may solvate target components of the feed gas stream, complex target components of the feed gas stream, and/or react with target components of the feed gas stream 104, where the target components include hydrogen sulfide and may include other sulfur containing compounds and carbon dioxide. In a preferred embodiment, the chemical treatment system is a regenerative chemical treatment system effective to solvate, complex, or react with one or more target components of the feed gas stream 104 to separate the target components from the feed gas stream 104, and from which the target components may subsequently be regenerated and separated. Separation unit 102 may include one or more units that consume thermal power and/or mechanical power and/or electrical power or combinations thereof for operation (for example, pumps, compressors, and other motor driven devices).

Separation unit 102 may include steam boilers and/or regenerative chemical treatment system reboilers. The water for the steam boilers and/or reboilers may be heated by the thermal power generated through combustion of the hydrogen sulfide stream 106. In some embodiments, the steam captured (thermal power) from combustion of the hydrogen sulfide stream 106 is used to generate low pressure steam for separation unit 102.

When feed gas separation unit 102 includes a regenerative chemical treatment system, the feed gas stream 104 is contacted with a composition that absorbs, solvates, complexes, or reacts with at least a majority of the hydrogen sulfide to form a composition or compound that contains the hydrogen sulfide or a composition or adduct formed by reaction of hydrogen sulfide with the contacting composition. If carbon dioxide is present in the feed gas stream 104, the composition may also solvate, complex, or react with at least a majority of the carbon dioxide in the feed gas stream to form a composition or compound that contains the carbon dioxide or a composition or adduct formed by reaction of carbon dioxide with the contacting composition.

The composition containing the hydrogen sulfide, and optionally carbon dioxide, and/or a complex, composition or adduct formed from the hydrogen sulfide and optionally carbon dioxide is regenerated after separation from contact with the feed gas stream 104 to regenerate the contacting composition and produce the hydrogen sulfide stream 106. Regeneration may be effected by application of thermal power to release the hydrogen sulfide stream 106 containing hydrogen sulfide, and carbon dioxide if present. The thermal power may be provided as steam. All of the thermal power necessary for regeneration of the composition for contact with the feed gas stream 104 may be provided by combustion of the hydrogen sulfide gas stream 106.

In an embodiment of the process of the present invention, when the feed gas stream 104 contains both hydrogen sulfide and carbon dioxide, the composition containing hydrogen sulfide and carbon dioxide, and/or a complex, composition, or adduct formed from hydrogen sulfide and/or carbon dioxide, may be regenerated so that carbon dioxide and hydrogen sulfide may be recovered separately. As noted above, carbon dioxide may be recovered separately from the hydrogen sulfide stream by temperature and/or pressure differential separation from the composition containing the hydrogen sulfide and carbon dioxide, and/or a complex, composition, or adduct formed therefrom. Separation unit 102 may include a separator structured and arranged to receive the composition containing the hydrogen sulfide and the carbon dioxide and to separate carbon dioxide and hydrogen sulfide individually from the composition by temperature and/or pressure differential separation. The carbon dioxide may be recovered separately from the hydrogen sulfide stream as a carbon dioxide stream (not shown). Alternatively, hydrogen sulfide and carbon dioxide may be recovered together from the composition to form the hydrogen sulfide stream 106.

The composition used in the chemical treatment system for contacting the feed gas stream 104 may be a liquid, solid and/or any material that may separate hydrogen sulfide, and optionally carbon dioxide, from the feed gas stream 104 and that may be regenerated to release hydrogen sulfide and carbon dioxide (if present in the feed gas stream 104). Such compositions include, but are not limited to, amines, sulfolane, water, methanol, ethylene glycol, diethylene glycol, triethylene glycol, n-methyl-2-pyrrolidinone, propylene carbonate, dimethyl ethers of polyethylene glycol, a mixture of compounds of general formula $CH_3O-(C_2H_4O)_nCH_3$ where n is an integer from about 2 to 9, or mixtures thereof.

In certain embodiments, the gas separation unit 102 includes a regenerative amine treatment unit for separation of the hydrogen sulfide stream 106 and the hydrocarbon gas stream 108 from the feed gas stream 104. Examples of amines used in a regenerative amine treatment unit include, but are not limited to, monoethanolamine, diethanolamine, triethanolamine, methyldiethanolamine, 2-(2-aminoethoxy)-ethanol, or di-isopropanolamine.

Examples of commercial chemical regenerative treatment processes that may be used in the process of the invention to separate the hydrogen sulfide stream 106 and the hydrocarbon gas stream 108 from the feed gas stream 104 include, but are not limited to, a Sulfinol gas treatment process, a Selexol (UOP™, Des Planes, Ill., USA) gas treatment process, a Rectisol® Process (Lurgi GmbH, Frankfurt Germany) and/or a Rectisol Wash Process (Linde Engineering, Germany).

The feed gas stream 104 may be treated in two or more separation processes in the feed gas separation unit 102 and/or may be recycled one or more times through a single separation process in the feed gas separation unit 102 to produce a hydrocarbon gas stream 108 with acceptable limits of hydrogen sulfide and acceptable limits of carbon dioxide for utilization or further treatment of the hydrocarbon gas stream 108 to provide a natural gas stream suitable for sale as a pipeline gas or for conversion into a compressed natural gas or a liquefied natural gas. The hydrocarbon gas stream preferably has a pressure of at least 1.7 MPa, or at least 3.4 MPa (500 psig), or at least 6.9 MPa (1000 psig).

The hydrocarbon gas stream 108 may be fed to a separation unit 114. The separation unit 114 may include one or more physical treatment systems, including but not limited to, a coalescing unit, a cyclone separator unit, an electrostatic precipitator unit, a fixed bed adsorption unit, a filter, a heat exchanger, a dehydration unit, a membrane unit, a pressure swing adsorption unit, a temperature separation unit; and/or one or more a chemical treatment units. In separation unit 114, water, metals, trace amounts of carbon oxides, trace amounts of hydrogen sulfide, natural gas liquids (e.g. $C_2$-$C_6$ hydrocarbons), and/or inert gases may be separated from the hydrocarbon gas stream 108 to form a natural gas stream 122 and/or a hydrocarbon containing stream suitable for sale as pipeline gas. "Carbon oxides," refers to compounds having carbon and oxygen bonds. Examples of carbon oxides include, but are not limited to, carbon dioxide, carbon monoxide, carbonyl sulfide or mixtures thereof.

For example, water may be removed from the hydrocarbon gas stream 108 in the separation unit 114 by passing the stream through a glycol dehydration system, a pressure swing adsorption unit, and/or a solid desiccant system. Metals (for example, mercury), if present, may be removed by contacting the dried hydrocarbon gas stream 108 with molecular sieves and/or activated carbon to remove a portion or substantially all of the metals from the hydrocarbon gas stream. In some embodiments, the metal content of the hydrocarbon gas stream 108 may be sufficiently low that removal of metals is not necessary.

The hydrocarbon gas stream 108 may be passed through a series of cryogenic units, absorption, and/or adsorption units to remove inert gases, for example nitrogen, and/or carbon oxides from the hydrocarbon gas stream. Residual carbon dioxide may be removed using the Catacarb® and/or Benfield gas treatment processes. The adsorption units and/or cryogenic units are, in some embodiments, a rectified adsorption and high pressure fractionation unit. In some embodiments, separation unit 114 includes a chemical treatment unit to remove trace amounts of hydrogen sulfide from the hydrocarbon gas stream 108. The trace amount of hydrogen sulfide removed from the hydrocarbon gas stream 108 in separation unit 114 may be combined with the hydrogen sulfide stream 106 exiting gas separation unit 102.

In some embodiments, the natural gas or pipeline gas stream 122 contains at most 50 ppm or at most 30 ppm or at most 10 ppm of hydrogen sulfide. Hydrogen sulfide content in the natural gas or pipeline gas stream 122 may be measured using ASTM Method D4804. The natural or pipeline gas stream 122 contains less hydrogen sulfide, by volume percent, than the feed gas stream 104.

In some embodiments, the hydrocarbon gas stream 108 is processed to separate hydrocarbons having a carbon number from 2 to 6 ($C_{2-6}$ hydrocarbons) from the hydrocarbon gas stream to form a natural gas liquids stream 120. Heavier hydrocarbons may be condensed from the hydrocarbon gas stream 108 by cooling the hydrocarbon gas stream 108 to a temperature below the dew point of such hydrocarbons, for example, in a heat exchanger. Alternatively, the hydrocarbon gas stream 108 may be processed in the separation unit 114 to separate $C_{2-6}$ hydrocarbons from the hydrocarbon gas stream by compressing the hydrocarbon gas stream 108, cooling the compressed hydrocarbon gas stream, and expanding the compressed cooled hydrocarbon gas stream to separate $C_{2-6}$ hydrocarbons from the hydrocarbon gas stream and produce natural gas. For example, the hydrocarbon gas stream 108 may be passed through a turboexpander/demethanizer system to produce a natural gas stream 122 and a natural gas liquids stream 120 containing $C_{2-6}$ hydrocarbons. The natural gas stream 122 produced from a turboexpander/demethanizer system may contain at least 50%, at least 70%, or at least 95% methane.

The natural gas stream 122 preferably has a pressure of at least 3.4 MPa (500 psig), where the pressure of the natural gas stream may be derived from the pressure of the feed gas stream 104 from a subsurface formation. If the natural gas stream 122 has a pressure below that which is required for pipelining the natural gas stream 122, the natural gas stream 122 may be compressed to a pressure of from 3.4 MPa to 12.1 MPa, as required by the pipeline into which the natural gas stream 122 is to be exported. The natural gas stream 122 may be compressed to the desired pressure, if necessary, by a compressor (not shown) that is powered by power derived from combustion of the hydrogen sulfide stream 106.

In some embodiments, the hydrocarbon gas stream 108 may be passed through a gas/liquid extraction system in the separation unit 114. In a gas/liquid extraction system the hydrocarbon gas stream 108 is contacted with an absorbing composition. The absorbing composition separates natural gas liquids ($C_{2-6}$ hydrocarbons) from the hydrocarbon gas stream 108 to form natural gas stream 122 and an absorbing composition/natural gas liquids stream 120. In some embodiments, the absorbing composition may be an oil, and the absorbing oil/natural gas liquids stream 120 may be distilled to produce ethane, propane, butane, pentane and/or hexane streams.

At least a portion of the natural gas produced in the separation unit 114 may be provided for further processing in a facility 124 as natural gas stream 126. In some embodiments, at least 99% of the natural gas exiting hydrocarbon separation unit 114 is provided as natural gas stream 126 for further processing in the facility 124.

The facility 124 includes one or more systems for processing the natural gas stream 126, and may include a compression system and/or a liquefaction system. The natural gas stream 126 may be compressed in a compression system in the facility 124 to a pressure of from 13.8 MPa to 27.6 MPA to form a compressed natural gas 130. Alternatively, the natural gas stream 126 may be liquefied in a liquefaction system in the facility 124 to produce a liquefied natural gas 128. Optionally, if the natural gas stream 126 is to be liquefied to produce LNG and has a pressure of less than 5.5 MPa or less than 6.3 MPa, the natural gas stream may be compressed in a compression system in the facility 124 to a pressure of at least 5.5 MPa or at least 6.3 MPa prior to being liquefied in the liquefaction system.

The natural gas stream 126 may be compressed in a compression system in the facility 124 using known compression methods. For example, the natural gas stream 126 may be compressed under isothermal, adiabatic, or polytrophic conditions. The natural gas stream 126 may be passed through one or more compressors. The compressors may be positive displacement and/or dynamic compressors. Examples of compressors include, but are not limited to, reciprocating, rotary, centrifugal and/or axial.

The natural gas stream 126, having a pressure of at least 5.5 MPa or at least 6.3 MPa, may be liquefied in a liquefaction system in the facility 124 using known liquefaction methods. For example, the natural gas stream 126 may be cooled through use of heat exchange and/or expansion to a temperature of below about $-160°$ C., or below about $-165°$ C., preferably to about $-162°$ C. to form liquefied natural gas 128. Examples of commercially available natural gas liquefaction systems and processes include, but are not limited to, the Air Products AP-X™ system the Shell DMR process, and the ConocoPhilips Cascade® process. The compressed natural gas 130 and/or liquefied natural gas 128 may be transported to other processing units and/or storage units.

The hydrogen sulfide stream 106 is provided from the feed gas separation unit 102 to a combustion unit 132. The hydrogen sulfide stream may contain at most 1% by volume, at most 0.1% by volume, or at most 0.01% by volume hydrocarbons including organosulfur species from the feed gas stream, as described in further detail above. The hydrogen sulfide stream 106 may include from above 0% to 40% by volume, from 1% to 30% by volume, or from 5% to 20% by volume carbon dioxide. In some embodiments, elemental sulfur may be combined with the hydrogen sulfide stream and/or provided to combustion unit 132.

An oxidant stream 134 comprising molecular oxygen is provided to the combustion unit 132 for combustion with the hydrogen sulfide stream 106. An oxygen enriched oxidant stream such as oxygen or enriched air is preferred when the hydrogen sulfide stream 106 comprises significant quantities of carbon dioxide. Air is a preferred oxidant stream when the hydrogen sulfide stream 106 is substantially free of carbon dioxide.

In the combustion unit 132, at least 34 mol % of the hydrogen sulfide in the hydrogen sulfide stream 106 is combusted with the oxidant stream 134, where oxidant stream and the hydrogen sulfide stream are provided for combustion at selected rates such that the molar ratio of molecular oxygen in the oxidant stream to be combusted relative to hydrogen sulfide in the hydrogen sulfide stream to be combusted is at least 1.4:1. The hydrogen sulfide stream 106 and/or the oxidant stream 134 may be provided to the combustion unit 132 at elevated pressure, for example via a forced draft fan and/or a combination of forced draft and induced draft fans, to circulate the gas streams in the combustion unit. The temperature in the combustion unit 132 may be controlled by controlling the flow rate of the oxidant stream 134 to the combustion unit 132, and/or the flow rate of the hydrogen sulfide stream 106 to the combustion unit 132, and/or by controlling the flow rate of a recycle stream of a combustion stream after recovery of thermal energy from the combusted gas. Combustion of at least a portion of the hydrogen sulfide stream 106 generates heat and a combustion stream formed of the combusted gas.

Combustion of at least a portion of the hydrogen sulfide stream 106 is preferably performed in the presence of a stoichiometric equivalent or a stoichiometric excess of molecular oxygen from the oxidant stream relative to the molar amount of hydrogen sulfide in the hydrogen sulfide stream. In embodiments when elemental sulfur is provided to combustion unit 132, the flow rate of the oxidant stream 134 may be adjusted to maintain a stoichiometric equivalent or a stoichiometric excess of molecular oxygen relative to the total amount of hydrogen sulfide in the hydrogen sulfide stream 106 and elemental sulfur supplied to combustion unit 132 such that substantially all, or all, of the hydrogen sulfide and elemental sulfur is converted to sulfur dioxide and water, and optionally small quantities of sulfur trioxide and sulfuric acid, in the combustion unit 132.

In some embodiments, the combustion stream resulting from the combustion of the hydrogen sulfide stream 106 includes a minimal amount or no hydrogen sulfide and a substantially equal molar mixture of sulfur dioxide and water as steam. The combustion stream may comprise 0%, or greater than 0% but less than 0.1%, or less than 0.05%, or less than 0.001% by volume of hydrogen sulfide. The combustion stream may include excess oxygen, one or more sulfur oxides, and steam, and may contain nitrogen if the oxidant stream is air or enriched air. The combustion of the hydrogen sulfide stream 106 generates 0 grams, or greater than 0 grams but at most 0.1 grams, or at most 0.01 grams, or at most 0.001 grams of carbon dioxide per gram of hydrocarbons in the feed gas stream 104. The combustion stream may also contain substantially all of the carbon dioxide separated from the feed gas stream, provided 1) that the feed gas stream contains carbon dioxide; and 2) that the carbon dioxide from the feed gas stream is not separated from the hydrogen sulfide from the feed gas stream prior to combusting the hydrogen sulfide stream.

The combustion stream is produced at a temperature ranging from 200° C. to 3000° C., or from 300° C. to 1500° C., or from 500° C. to 1000° C. Heat from the combustion stream may be generated at a rate such that the thermal power captured from the heat of the combustion stream is sufficient to produce all of the power (thermal, mechanical, and/or electrical) necessary to operate all the processes and systems used in separation unit 102, separation unit 114, and compression/liquefaction unit 124. The thermal power captured from the heat of the combustion stream may be thermally and mechanically and electrically integrated with the processes used to produce natural gas and/or compressed natural gas and/or liquefied natural gas, and/or liquefied carbon dioxide and/or sulfur dioxide.

Thermal power captured from the heat of the combustion stream formed in the combustion unit 132 is captured in thermal power unit 140. Combustion unit 132 and thermal power unit 140 may be an integrated unit or separate units. In a preferred embodiment thermal power is captured as steam in the thermal power unit 140. Thermal power unit 140 may include one or more heat exchangers and/or one or more steam manufacture units such as a steam boiler.

The thermal power unit 140 may capture thermal power from the combustion stream as steam. All or substantially all of the thermal power from combustion of the hydrogen sulfide stream 106 may be used to generate steam at pressures ranging from 0.34 MPa to 34.5 MPa, or from 3.4 MPa to 34.5 MPa, or from 13.8 MPa to 34.5 MPa, or from 22.2 MPa to 34.5 MPa, or from 30 MPa to 34.5 MPa; and temperatures ranging from 135° C. to 650° C., or from 240° C. to 650° C., or from 335° C. to 650° C., or from 375° C. to 650° C.

The thermal power unit 140 may be designed and utilized to produce steam of various grades, based on the temperature and pressure of the steam. Saturated steam, superheated steam, supercritical steam, and/or ultra supercritical steam may each be generated in separate sections of the thermal power unit 140.

At least a portion of the thermal power generated by combustion of the hydrogen sulfide stream may be converted to mechanical and/or electric power or may be provided to units in the system 100 as thermal power. The various grades of steam that may be produced in the thermal power unit 140 may be utilized to provide thermal power to the process and to generate mechanical and/or electrical power. Steam produced in the thermal power unit 140 from the heat of the combustion stream may be provided to a steam turbine unit 142 via conduit 144 for the generation of mechanical and/or electrical power, and/or to steam powered units in separation unit 102 via conduit 146, and/or to steam powered units in separation unit 114 via conduit 148, and/or and to steam powered compression and/or liquefaction units in facility 124 via conduit 150. Steam powered units include, but are not limited to, pumps in chemical treatment systems, natural gas compressors, carbon dioxide liquefaction compressors, refrigeration compressors, and electrical generators.

Low pressure saturated steam may be used to provide thermal power to re-boilers of chemical treatment systems of separation unit 102 and/or separation unit 114. High pressure saturated and/or superheated and/or supercritical steam may be used to provide mechanical power to equipment used in separation unit 102 and/or separation unit 114 and/or facility 124, for example by passing the high pressure saturated, and/or superheated and/or supercritical steam through a steam expansion device (i.e., a steam turboexpander or a steam turbine) to generate mechanical (shaft) power. Superheated steam, more preferably supercritical steam, and most preferably ultra supercritical steam may be utilized to generate electrical power, for example, by passing the steam through a steam expansion device (e.g. a steam turboexpander or a steam turbine) coupled with an electrical power generator.

In some embodiments, at least 75%, or at least 85%, or at least 90% of the thermal power produced by combusting the hydrogen sulfide stream 106 is used to make electrical power using steam turbines. Ultra supercritical or supercritical steam 144 may be provided to steam turbine unit 142. The ultra supercritical or supercritical steam may be used to drive electrical generators in steam turbine unit 142 to meet the electrical power requirements of separating the feed gas stream 104 into the hydrogen sulfide stream 106 and the hydrocarbon gas stream 108 and for processing the hydrocarbon gas stream 108 to produce natural gas, compressed natural gas, or LNG. The steam turbine unit 142 may convert thermal power from the ultra supercritical or supercritical steam 146 into all the electrical power necessary to process the hydrocarbon gas stream 108 and to separate the hydrogen sulfide stream 106 and the hydrocarbon gas stream 108 from the feed gas stream 104 (for example, all the electrical power required for the operation of separation unit 102, separation unit 114, and/or facility 124).

The steam turbine unit 142 may include one or more electrical generators and/or one or more steam turbines. Steam turbine unit 142 may be a multi-stage turbine (for example, a steam turbine may include at least one high-pressure stage, at least one medium pressure stage, at least one low pressure stage, or combinations thereof). In some embodiments, the steam turbine unit 142 is electrically integrated with the separation unit 102, the separation unit 114, and/or facility 124. The steam turbine unit 142 may be electrically integrated with a power grid for export of electrical power to the power grid by electrical line 152.

In a preferred embodiment, all the thermal power from the combustion of the hydrogen sulfide stream 106 is captured as steam. Sufficient heat is provided to the thermal power unit 140 from the combustion of the hydrogen sulfide stream 106 such that the temperature of water in one or more boilers in the thermal power unit 140 is raised to make steam and/or maintain steam production. At least a portion of the steam may be used to generate all of the mechanical, electrical, and thermal power required for processes to produce natural gas, compressed natural gas, liquefied natural gas, and/or to operate other surface facility processes. The steam turbine unit 142 may provide electrical power to the processing units and/or separating units 102, 114 and 124 and/or may be exported via line 152. Electrical power may be supplied to separation unit 102 via electrical line 154, and/or to separation unit 114 via electrical line 156, and/or to facility 124 via line 158. The electrical power provided may be sufficient: (a) for all of the electrical power required for separation of the feed gas stream (for example, for the operation of the feed gas separation unit 102 to separate the feed gas stream 104 into the hydrogen sulfide stream 106 and the hydrocarbon gas stream 108); (b) for the processing of the hydrocarbon gas stream 108 into natural gas, compressed natural gas, or LNG (for example, for the operation of the separation unit 114, and, optionally, compression and/or liquefaction systems in facility 124); and may be sufficient (c) for sale or use in other electrical power consumption units.

Other electrical power consumption units that may be powered by electrical power produced by the system 100 include, but are not limited to, power distribution grids, server farms, industrial electric smelters, or combinations thereof. In some embodiments, the other electrical power consumption units are located on or near a body of water, for example, server farms located on a floating or anchored platform on a body of water. Smelters may include, but are not limited to, aluminum smelters.

After thermal power has been captured from the heat of the combustion stream in the thermal power unit 140, a cooled combustion stream 136 may be provided from the thermal power unit 140 to a sulfur dioxide separator 138. In the sulfur dioxide separator 138 the cooled combustion stream 136 may be separated into a sulfur dioxide stream and a water stream and, if inert gases are present in the cooled combustion stream, an inert gas stream. Water may be separated from sulfur dioxide and the cooled combustion stream 136 in the sulfur dioxide separator 138 by adjusting the temperature and pressure of the cooled combustion stream 136 so that water condenses out of the cooled combustion stream. Sulfur dioxide may be separated from the cooled combustion stream 136 or a dehydrated cooled combustion stream by contacting the cooled combustion stream or dehydrated cooled combustion stream with concentrated sulfuric acid.

To separate water from the cooled combustion stream 136, the cooled combustion stream may be further cooled, and, if necessary, expanded to reduce the pressure of the combustion stream, within the sulfur dioxide separator 138 to a temperature and pressure at which water separates from the cooled combustion stream. For example, in the sulfur dioxide separator 138 the cooled combustion stream 136 may be further cooled to a temperature ranging from about −5° C. to about 85° C. and the pressure of the stream may be adjusted, if necessary, to a pressure of from 0.1 MPa to 0.2 MPa to separate water from sulfur dioxide and unreacted oxidant and inert gases. The water produced in the sulfur dioxide separator 138 may be supplied to the thermal power unit 140 via conduit 160 for use in producing steam, and/or may be supplied directly to the steam turbine 142 via conduit 162, and/or may be mixed with steam from thermal power unit 140 via conduit 164.

In the sulfur dioxide separator 138, sulfur dioxide may be separated from the cooled combustion stream 136 or the dehydrated cooled combustion stream by contacting the stream with a material and/or compound that adsorbs at least a portion of the sulfur dioxide from the stream. The adsorbent may be treated to release the sulfur dioxide to form a purified sulfur dioxide stream. In some embodiments, the sulfur dioxide stream is separated from other components in the cooled combustion stream 136 (for example, inert gases, carbon oxides and/or water) by mixing the cooled combustion stream or the dehydrated cooled combustion stream with aqueous inorganic salt solutions, aqueous organic salt solutions, amines, aqueous alcohol solutions, ethers and/or poly glycol solutions. A commercially available sulfur dioxide separation system that may be utilized to separate sulfur dioxide from the cooled combustion stream 136 or the dehydrated cooled combustion stream is a Cansolv® $SO_2$ Scrubbing System (available from Shell Global Solutions (US), Inc. Houston, Tex.

The sulfur dioxide stream 166 separated from the cooled combustion stream 136 or the dehydrated cooled combustion stream may exit the sulfur dioxide separator 138 as a gas, a compressed gas and/or a liquid. The sulfur dioxide stream 166 may include sulfur dioxide and some sulfur trioxide. In some embodiments, the sulfur dioxide stream 166 contains at least 50% by volume, at least 80% by volume, or at least 99% by volume of sulfur dioxide. Sulfur dioxide content in a stream may be measured using ISO Method 7935. The sulfur dioxide stream 166 may be stored and/or combined with one or more streams to form a concentrated sulfur dioxide stream.

In some embodiments of the process of the present invention, the sulfur dioxide stream 166 may be dried, compressed and/or liquefied. The sulfur dioxide stream 166 may be dried through contact of the sulfur dioxide stream 166 with concentrated sulfuric acid at 30° C. to form a dried sulfur dioxide stream. The dried sulfur dioxide stream may be compressed using a compressor working between 0.38 MPa and 0.5 MPa to form compressed sulfur dioxide. The compressed sulfur dioxide may be cooled to −30° C. to −60° C. to form a liquefied sulfur dioxide stream. The thermal power generated from combustion of the hydrogen sulfide stream 106 may be utilized to generate all of the thermal and/or electrical and/or mechanical power required to dry, compress and liquefy the sulfur dioxide stream 166 and all the thermal, and/or electrical, and/or mechanical power for the separation of the feed gas stream 104 into the hydrogen sulfide stream 106 and the hydrocarbon gas stream 108 and for the processing of the hydrocarbon gas stream 108.

In some embodiments, the sulfur dioxide in the sulfur dioxide stream 166 may be converted to sulfuric acid. Purification of sulfur dioxide and subsequent sulfuric acid production is described in U.S. Pat. No. 5,389,354 to Brandle et al.; U.S. Pat. No. 4,659,556 to Eros; U.S. Pat. No. 4,213,958 to Cameron et al.; and U.S. Pat. No. 3,475,120 to Mauer et al. The sulfuric acid may be made at the same facility as the production of natural gas, compressed natural gas, and/or liquefied natural gas or at a remote location. When the sulfuric acid is produced at the production facility for natural gas, compressed natural gas and/or liquefied natural gas, the thermal power generated by combustion of the hydrogen sulfide stream 106 is sufficient to generate all the necessary mechanical and/or electrical and/or thermal power required for producing the sulfuric acid and all the thermal and/or mechanical and/or electrical power for the separation of the feed gas stream 104 into the hydrogen sulfide stream 106 and the hydrocarbon gas stream 108 and for the processing of the hydrocarbon gas stream 108.

In some embodiments, carbon dioxide may be separated from the cooled combustion stream 136 or the dehydrated cooled combustion stream in the sulfur dioxide separator 138. The carbon dioxide in the cooled combustion stream 136 may be carbon dioxide that was present in the feed gas stream 104 and was carried through the process into the cooled combustion stream 136 and/or may be carbon dioxide formed by the combustion of hydrocarbons present in the hydrogen sulfide stream 106 (e.g. mercaptans and thiophenes). The separated carbon dioxide may be sequestered, treated, sold, introduced in a subterranean formation as a drive or displacement fluid and/or combined with other carbon oxides streams. The carbon dioxide may be compressed and/or liquefied, and then pumped into a hydrocarbon formation, a storage facility and/or a transportation unit.

Figure 2:
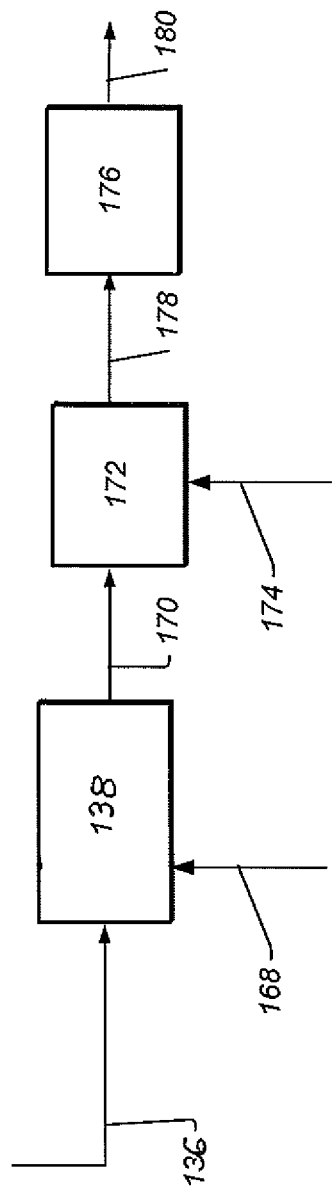
FIG. 2 depicts a schematic of an embodiment of production of sulfuric acid from a feed gas stream containing significant quantities of hydrogen sulfide.

FIG. 2 depicts a schematic representation of an embodiment of production of sulfuric acid from a feed gas stream high in hydrogen sulfide. In FIG. 2, the feed gas stream is treated as described in FIG. 1 to produce a cooled combustion gas 136. In some embodiments, concentrated sulfuric acid (e.g. a 90% to 100% by weight sulfuric acid solution) is used as a separating composition to separate the sulfur dioxide from the cooled combustion stream 136. A concentrated sulfuric acid stream 168, or other separating composition, is provided to the sulfur dioxide separator 138 to be contacted with the cooled combustion stream 136. Water is adsorbed from the cooled combustion stream 136 by contacting the cooled combustion stream 136 with the concentrated sulfuric acid stream 168, producing a dehydrated cooled combustion stream 170. The dehydrated cooled combustion stream 170 may include sulfuric acid, sulfur dioxide, molecular oxygen, nitrogen and/or one or more nitrogen oxides, and may also include carbon dioxide. The dehydrated cooled combustion stream 170 exits sulfur dioxide separator 138 and enters oxidizing unit 172. In oxidizing unit 172, the dehydrated cooled combustion stream 170 is contacted with one or more catalysts to produce a sulfur trioxide stream. If sufficient molecular oxygen is not present in the dehydrated cooled combustion stream to oxidize the sulfur dioxide therein to form sulfur trioxide, a molecular oxygen stream 174 may be provided to the oxidizing unit 172. The one or more catalysts may include any catalyst that is effective to catalyze the oxidation of sulfur dioxide to sulfur trioxide, for example, a vanadium (V) oxide catalyst. The dehydrated cooled combustion stream may be contacted with the one or more oxidizing catalysts, and optionally the molecular oxygen stream 174, in the oxidizing unit 172 at temperatures ranging from 400° C. to 500° C. to effect the oxidation. The dehydrated cooled combustion stream 170 may be heated prior to being fed to the oxidizing unit 172.

A sulfur trioxide stream 178 produced in the oxidizing unit 172 exits the oxidizing unit 172 and enters an absorption unit 176. In the absorption unit 176, the sulfur trioxide stream 178 is contacted with sufficient water to hydrate the sulfur trioxide and thereby form a concentrated sulfuric acid solution (for example, 90 wt % to 100 wt % sulfuric acid solution). A concentrated sulfuric acid solution stream 180 exits absorption unit 176 for storage and/or transportation. In some embodiments, the sulfuric acid is suitable for use in the production of phosphoric acid.

To facilitate a better understanding of the present invention, the following examples of are provided. In no way should the following examples be read to limit, or define, the scope of the invention.

EXAMPLES

In the following examples, power required to compress natural gas and/or a hydrocarbon gas stream was estimated based on data presented in, "Natural Gas Compressor Station in the Interstate Pipeline Network: Development Since 1996" by James Tobin. This document is available to the general public from the Energy Information Administration of the United States Department of Energy, Office of Oil and Gas, November 2007. The compression power estimate was based on information from footnote 6 wherein it is stated that for 1,000 compression stations where intake and outtake pressure were available, the average ramp up pressure per station was 250 psig (pounds per square inch gauge). Additionally, it was stated that the highest discharge pressure ranged from 1,500 to 1,750 psig, primarily to 42-inch and 36-inch diameter pipelines. Additionally, information from Table 1 was used in the power calculations. Specifically, the stated "Total Throughput Rating" of 881,472 MMcf/d (2006) and the stated "Total Installed Horsepower" (2006) of 16,880,345 HP were used in the power estimate calculations. Based on the information presented, the power to compress 1 MMscf/d natural gas by an incremental pressure increase of 250 psig was estimated at to be 19.15 $HP_{mechanical}$ or 0.0143 $MW_{mechanical}$. Additionally, it was assumed that a steam turboexpander would be used to provide the mechanical drive for the compressor and that the efficiency of the steam expander for conversion of thermal power to mechanical power was 80% meaning that 19.15 $HP_{mechanical}$ is produced at a cost of 0.0179 MWt.

In the examples related to producing LNG, the power required to compress 56.443 MMscf/h of natural gas having a pressure of 1.7 MPa (250 psig) to a pressure of 6.3 MPa (1000 psig) for liquefaction in three incremental steps of 1.7 MPa (250 psig) each was calculated utilizing the above values according to the following formula:

$$\left\{ \frac{\left[ \left( \frac{0.0179 \text{ MWt}}{\frac{1 MMscf}{d}} \right) \times \left( \frac{24 \text{ h}}{d} \right) \times \left( \frac{56.433 MMscf}{h} \right) \right]}{\Delta P \text{ unit 250 } psi} \right\} \times 3 \Delta P \text{ units 250 } psi =$$

$$72.7 \text{ MWt.}$$

The calculated power was 72.7 MW$_t$. Similarly, in the examples related to producing a pipeline gas, the power required to compress 56.443 MMscf/h of natural gas having a pressure of 1.7 MPa to a pressure of 12.1 MPa (1750 psig) to make pipeline natural gas in 6 incremental steps of 1.7 MPa each was calculated to be 145.5 MWt. Similarly, in the examples related to producing a compressed natural gas, the power required to compress 56.433 MMscf/h of natural gas having a pressure of 1.7 MPa to a pressure of 24.1 MPa (3500 psig) in 13 incremental steps of 1.7 MPa each to make compressed natural gas was calculated to be 315.2 MW$_t$.

Also in the following examples that are directed to producing a liquefied natural gas, the liquefaction power required to liquefy a natural gas stream supplied at approximately 6.8 MPa [1,000 psig (920 psia)] was estimated using data from SRI Consulting Process Economics Program Report 103A LIQUEFIED NATURAL GAS, November 2004, authored by Marcos Cesar based on an average power calculated from three liquefaction processes, the Triple Mixed Refrigerant Process, the Double Mixed Refrigerant Process, and the Single Mixed Refrigerant Process. The liquefaction power was estimated by averaging the liquefaction power required to liquefy a metric ton of natural gas The liquefaction power requirement per metric ton of natural gas at 6.34 MPa (920 psia) was reported to be 261 kWh per metric ton LNG using the Triple Mixed Refrigerant Process (Table 5.1 of Report 103A). Similarly, the liquefaction power requirement per metric ton of natural gas at 6.34 MPa was reported to be 283 kWh per metric ton LNG using the Dual Mixed Refrigerant Process (Table 6.1 of Report 103A). The liquefaction power requirement per metric ton of natural gas at 6.34 MPa was reported to be 323 kWh per metric ton LNG using the Single Mixed Refrigerant Process (Table 7.1 of Report 103A). The estimated power requirement for liquefaction natural gas was calculated to be 289 kWh per metric ton LNG, the average of the three power requirements. The calculated power requirement was multiplied by 2 to convert it from MWe basis to MWt basis, assuming that electric power is produced at 50% thermal efficiency. Thus, the power requirement for liquefaction of natural gas at 6.8 MPa (1,000 psig) was estimated to be approximately 578 kWht per metric ton LNG produced.

The thermal power required for liquefaction of 1142 metric tons per hour of natural gas supplied at 6.8 MPa may be estimated as follows:

$$578 \frac{\text{kWht}}{\text{mT}} \times \frac{\text{MWht}}{1000 \text{ kWht}} \times 1142 \frac{\text{mT}}{\text{h}} = 660 \text{ MWt}$$

Examples 1 to 11

In a process model using process steps in accordance with a process of the present invention, power calculations for the production of 1142 metric tons of liquid natural gas (LNG) per hour from selected feed gas streams containing methane and from 5% to 95% by volume hydrogen sulfide and having a pressure of 1.7 MPa (250 psig) were performed using energy consumption data obtained from known refinery processes. In the process model, a selected feed gas stream was treated to separate water and liquid hydrocarbons from the feed gas stream. Next, hydrogen sulfide was removed from the feed gas stream using an amine extraction system to produce a hydrocarbon gas stream containing the methane. The power required to regenerate hydrogen sulfide from the hydrogen sulfide-loaded amine system was supplied as steam produced in a boiler. The boiler was assumed to have 100% thermal efficiency. In the process model, the thermal power for the boiler was produced by combusting the entire recovered hydrogen sulfide stream with an oxidant containing molecular oxygen, wherein the molar ratio of the molecular oxygen to the hydrogen sulfide in the combustion was 1.5:1. The lower heating value of 6545 Btu per pound (15213 kilojoule per kilogram) of hydrogen sulfide was used in the calculations. A heating value for the regeneration of hydrogen sulfide from the hydrogen sulfide loaded amine extraction solution of 4030 Btu per pound (9374 kilojoule per kilogram) of hydrogen sulfide produced was used in the calculations. In the process model, if supplemental power was necessary, methane was used as fuel. In the calculations, the consumption of methane was estimated using the lower heating value of 21433 Btu per pound (49820 kilojoule per kilogram) of methane.

In the process model, the hydrocarbon gas stream produced by separation of hydrogen sulfide from the feed gas stream is processed to produce LNG. Power intensive steps included in the process model for processing the hydrocarbon gas stream to form the LNG were 1) compressing the hydrocarbon gas stream from a pressure of 1.7 MPa to form a compressed natural gas having a pressure of 6.9 MPa (1000 psig); and 2) liquefying the compressed natural gas to form LNG. Other steps included in forming LNG such as separating heavier hydrocarbons from the hydrocarbon gas stream, removing metals from the hydrocarbon gas stream, dehydrating the hydrocarbon gas stream, and separating non-hydrocarbon gases from the hydrocarbon gas stream were excluded from the process model from an energy/power perspective since the power required to effect these steps is very small relative to the power required to effect the steps of separating/regenerating hydrogen sulfide using an amine system, compressing the hydrocarbon gas stream to form a compressed natural gas, and liquefying the compressed natural gas. In the process model, the thermal power required to compress and liquefy the hydrocarbon gas stream was provided from the boiler in which the hydrogen sulfide was combusted.

Figure 3:
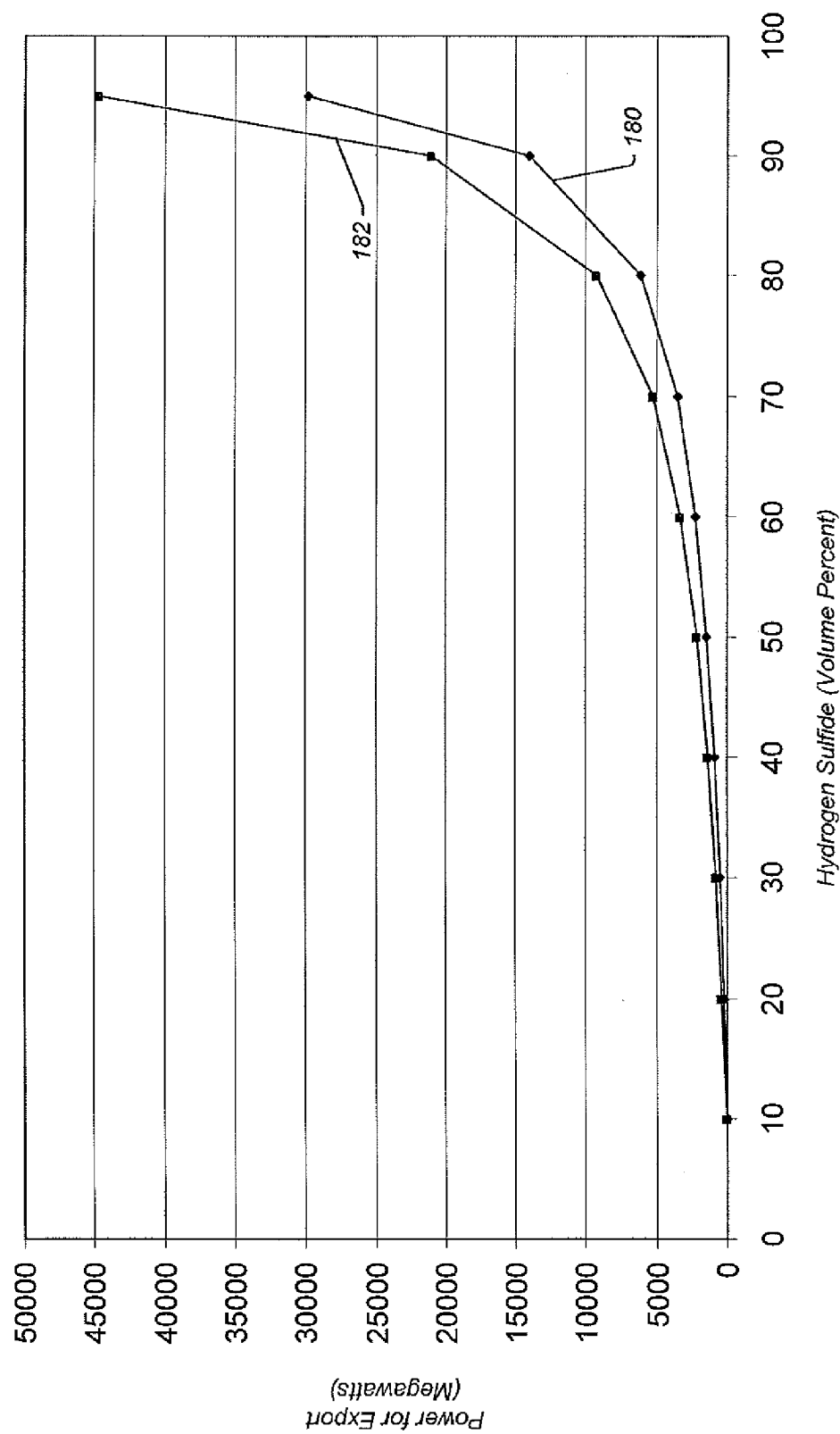
FIG. 3 depicts an example of a plot of power available for export, as electricity, in megawatts (MWe) versus volume percent of hydrogen sulfide content of a gas stream utilizing a process in accordance with the present invention.

TABLE 1 lists power data, LNG production data, sulfur dioxide production data, and carbon dioxide emission data from the selected feed gas streams. FIG. 3 depicts an example of a plot of the amount of power available for export (MW) versus hydrogen sulfide content during the production of LNG at a rate of 1142 mT/h (10 million metric tons of LNG per calendar year) for the feed stream compositions listed in TABLE 1. Data 180 represents electric power available for export at 40% thermal efficiency. Data 182 represents electric power available for export at 60% thermal efficiency.

TABLE 1

| Illustrative Example No. | 1 | 2 | 3 | 4 | 5 | 6 | 7 | 8 | 9 | 10 | 11 |
|---|---|---|---|---|---|---|---|---|---|---|---|
| Volume %, $H_2S$ | 5 | 10 | 20 | 30 | 40 | 50 | 60 | 70 | 80 | 90 | 95 |
| Volume %, $CH_4$ | 95 | 90 | 80 | 70 | 60 | 50 | 40 | 30 | 20 | 10 | 5 |
| LNG Produced, mT/h | 1142 | 1142 | 1142 | 1142 | 1142 | 1142 | 1142 | 1142 | 1142 | 1142 | 1142 |
| Sulfur Dioxide Produced, mT/h | 240 | 507 | 1142 | 1957 | 3044 | 4566 | 6849 | 10654 | 18265 | 41096 | 86758 |
| Power Generated By $H_2S$ Burning, MWt | 540 | 1139 | 2563 | 4394 | 6835 | 10253 | 15380 | 23924 | 41012 | 92278 | 194809 |
| Power Required To Separate $H_2S$, MWt | 332 | 702 | 1579 | 2707 | 4211 | 6317 | 9475 | 14739 | 25267 | 56850 | 120016 |
| Excess Power After Purifying Natural Gas, MWt | 207 | 437 | 984 | 1687 | 2624 | 3936 | 5905 | 9185 | 15746 | 35428 | 74793 |
| Power to Compress Natural Gas to 6.8 MPa (1,000 psig), MWt | 73 | 73 | 73 | 73 | 73 | 73 | 73 | 73 | 73 | 73 | 73 |
| Liquefaction Power Required To Make LNG, MWt | 660 | 660 | 660 | 660 | 660 | 660 | 660 | 660 | 660 | 660 | 660 |
| Excess Power Produced After Making LNG, MWt | 0 | 0 | 251 | 954 | 1892 | 3204 | 5172 | 8452 | 15013 | 34695 | 74060 |
| Power Export at 40% Efficiency After Making LNG, MWe | 0 | 0 | 101 | 382 | 757 | 1281 | 2069 | 3381 | 6005 | 13878 | 29624 |
| Power Export at 60% Efficiency After Making LNG, MWe | 0 | 0 | 151 | 573 | 1135 | 1922 | 3103 | 5071 | 9008 | 20817 | 44436 |
| Power Exported After Making LNG, kWh/kg $H_2S$ | 0 | 0 | 0.4 | 0.9 | 1.2 | 1.3 | 1.4 | 1.5 | 1.5 | 1.6 | 1.6 |
| Supplemental Power Required, MWt | 526 | 295 | 0 | 0 | 0 | 0 | 0 | 0 | 0 | 0 | 0 |
| Methane Required for Supplemental Power, mT/h | 38 | 21 | 0 | 0 | 0 | 0 | 0 | 0 | 0 | 0 | 0 |
| Carbon Dioxide Emitted, mT/h | 104 | 59 | 0 | 0 | 0 | 0 | 0 | 0 | 0 | 0 | 0 |

Using the values in TABLE 1, the maximum amount of thermal power available upon separation and combustion of hydrogen sulfide from the selected feed gas streams (basis production of 1142 metric tons of LNG per hour from the feed gas streams) was calculated to be 207 MWt at 5% $H_2S$, 437 MWt at 10% $H_2S$, 984 MWt at 20% $H_2S$, 1687 MWt at 30% $H_2S$, 2624 MWt at 40% $H_2S$, 3936 MWt at 50% $H_2S$, 5905 MWt at 60% $H_2S$, 9185 MWt at 70% $H_2S$, 15746 MWt at 80% $H_2S$, 35428 MWt at 90% $H_2S$, and 74793 MWt at 95% $H_2S$ [available thermal power=thermal power generated by combustion of separated hydrogen sulfide minus thermal power consumed to separate hydrogen sulfide from the feed gas stream]. The amount of excess thermal power generated by combusting hydrogen sulfide from the selected feed gas streams containing methane and from 20%-95% hydrogen sulfide and providing a portion of the thermal power produced thereby sufficient to separate the hydrogen sulfide from the feed gas stream to produce a methane-containing hydrocarbon gas stream and to process the hydrocarbon gas stream to produce liquefied natural gas (basis production of 1142 metric tons of LNG per hour) was calculated to be 251 MWt at 20% $H_2S$, 954 MWt at 30% $H_2S$, 1892 MWt at 40% $H_2S$, 3204 MWt at 50% $H_2S$, 5172 MWt at 60% $H_2S$, 8452 MWt at 70% $H_2S$, 15013 MWt at 80% $H_2S$, 34695 MWt at 90% $H_2S$, and 74060 MWt at 95% $H_2S$ [excess thermal power= (thermal power generated from combustion of separated hydrogen sulfide) minus (thermal power consumed to separate hydrogen sulfide and methane from the feed gas stream plus thermal power consumed to compress the separated methane plus thermal power consumed to liquefy the compressed methane to produce LNG)].

The data in Examples 1 to 11 demonstrate generation of thermal power from combustion of a hydrogen sulfide stream with an oxidant at a molar ratio of molecular oxygen to hydrogen sulfide of 1.5:1, where the hydrogen sulfide stream is separated from a feed gas stream containing hydrocarbons and at least 20 vol. % hydrogen sulfide, where a hydrocarbon gas stream is also separated from the feed gas stream and the hydrocarbon gas stream is processed to produce LNG, and where the thermal power is utilized in the steps of separating the feed gas stream into the hydrogen sulfide stream and the hydrocarbon gas stream and processing the hydrocarbon gas stream to produce LNG.

The data in Examples 1 to 11 also demonstrate generation of thermal power from combustion of more than one third of a hydrogen sulfide stream with an oxidant at a molar ratio of molecular oxygen to hydrogen sulfide of 1.5 to 1, where the hydrogen sulfide stream is separated from a feed gas stream containing hydrocarbons and at least 5 vol. % hydrogen sulfide, where a hydrocarbon gas stream is also separated from the feed gas stream and the hydrocarbon gas stream is processed to produce LNG.

Furthermore, the data in Examples 1 to 11 demonstrates that the process of the present invention utilizing a feed gas stream containing hydrocarbons and at least 20 vol. % hydrogen sulfide generates over 2500 $MW_t$ of thermal power, of which over 250 $MW_t$ of thermal power is generated in excess of the power required to separate the feed gas stream into a hydrocarbon gas stream and a hydrogen sulfide stream and to process the hydrocarbon gas stream to produce LNG. Upon conversion of the excess thermal power to electrical power, at least 100 megawatts of electric power is available for export as electricity at a 40% efficiency while at most 0.1 grams of carbon dioxide per gram of hydrocarbons in the feed gas stream are produced during combustion of the hydrogen sulfide.

Comparative Examples 12 to 22

In a process model using process steps in accordance with the production of LNG using a conventional Claus process, power calculations for the production of 1142 metric tons of LNG per hour from selected feed gas streams containing methane and from 0% to 95% hydrogen sulfide and having a pressure of 1.7 MPa (250 psig) were performed using energy consumption data obtained from a known refinery process. In the process model, the feed gas stream was treated to separate water and liquid hydrocarbons from the feed gas stream. Next, hydrogen sulfide was removed from the feed gas stream using an amine extraction system to produce a hydrocarbon gas stream containing the methane. In the process model, thermal power required to regenerate hydrogen sulfide from the hydrogen sulfide loaded amine system was supplied as steam produced from Claus Process heat recovery unit(s) and operation of a supplemental boiler that was fueled by natural gas produced in the process. The boiler was assumed to have 100% thermal efficiency. In the process model, hydrogen sulfide produced from regeneration of the amine system was converted to elemental sulfur via the Claus Process. A heating value of 2973 Btu per pound (6915 kilojoule per kilogram) of elemental sulfur produced from the Claus Process was used in the calculations. A heating value for the regeneration of the hydrogen sulfide loaded amine extraction solution of 4030 Btu per pound (9374 kilojoule per kilogram) of hydrogen sulfide produced was used in the calculations. In the process model, methane was used as fuel for generating supplemental power. The consumption of methane was estimated using the lower heating value of 21433 Btu per pound (49820 kilojoule per kilogram) of methane.

In the process model, the hydrocarbon gas stream produced by separation of the hydrogen sulfide stream from the feed gas stream is processed to produce LNG. Power intensive steps included in the process model for processing the hydrocarbon gas stream to form the LNG were 1) compressing the hydrocarbon gas stream having a pressure of 1.7 MPa to form a compressed natural gas having a pressure of 6.9 MPa; and 2) liquefying the compressed natural gas to form LNG. Other steps included in forming LNG such as separating heavier hydrocarbons from the hydrocarbon gas stream, removing metals from the hydrocarbon gas stream, dehydrating the hydrocarbon gas stream, and separating non-hydrocarbon gases from the hydrocarbon gas stream were excluded from the process model from an energy/power perspective since the power required to effect these steps is very small relative to the power required to effect the steps of separating/regenerating hydrogen sulfide using an amine system, compressing the hydrocarbon gas stream to form a compressed natural gas, and liquefying the compressed natural gas. In the process model, the thermal power required to compress and liquefy the hydrocarbon gas stream was provided from the Claus process heat recovery unit(s) and, if necessary, the supplemental boiler in which the natural gas produced by the process was burned.

Figure 4:
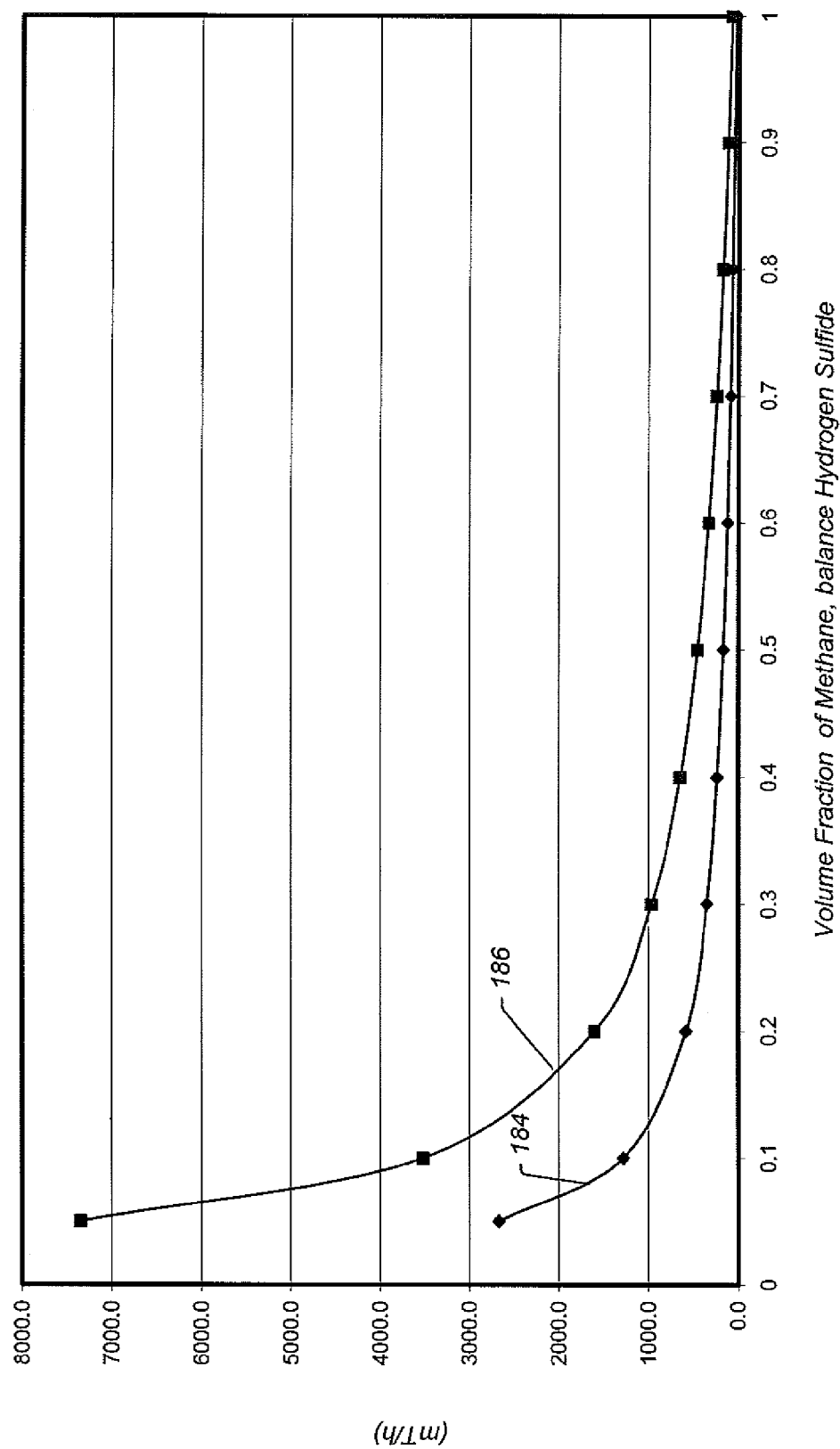
FIG. 4 depicts an example of a plot of methane consumed in metric tons per hour (mT/h) and carbon dioxide emitted in metric tons per hour (mT/h) versus volume fraction of methane, with the balance being hydrogen sulfide, for liquefaction of 10 million metric tons per calendar year of methane using a prior art Claus process.

TABLE 2 lists power data, LNG production data, elemental sulfur production data, and carbon dioxide emission data for the production of LNG from the selected feed gas streams utilizing the conventional Claus process. FIG. 4 is a plot of methane consumed (mT/h) and carbon dioxide emitted (mT/h) versus volume fraction of methane with the balance being hydrogen sulfide during the production of LNG at a rate of 1142 mT/h (10 million metric ton of LNG per calendar year) for the feed stream compositions listed in TABLE 2. In FIG. 4, data 184 represents methane consumed in metric tons per hour (mT/h) sufficient to provide required supplemental power to operate the process, relative to the volume fraction of methane in the feed gas stream. Data 186 represents carbon dioxide emitted in metric tons per hour (mT/h) when supplemental methane is provided in an amount sufficient to provide required supplemental power to operate the process, relative to the volume fraction of methane in the feed gas stream. As shown in TABLE 2 and FIG. 4, the amount of methane fuel required for supplemental power for hydrogen sulfide separation and to produce LNG increases significantly as the amount of hydrogen sulfide in the feed stream increases.

TABLE 2

| Comparative Example No. | 12 | 13 | 14 | 15 | 16 | 17 | 18 | 19 | 20 | 21 | 22 |
|---|---|---|---|---|---|---|---|---|---|---|---|
| Volume %, $H_2S$ | 0 | 10 | 20 | 30 | 40 | 50 | 60 | 70 | 80 | 90 | 95 |
| Volume %, $CH_4$ | 100 | 90 | 80 | 70 | 60 | 50 | 40 | 30 | 20 | 10 | 5 |
| LNG Produced, mT/h | 1142 | 1142 | 1142 | 1142 | 1142 | 1142 | 1142 | 1142 | 1142 | 1142 | 1142 |
| Elemental Sulfur Produced, mT/h | 0 | 254 | 571 | 978 | 1522 | 2283 | 3425 | 5327 | 9132 | 20548 | 43379 |
| Power Generated By Claus Plant, MWt | 0 | 487 | 1096 | 1879 | 2922 | 4383 | 6575 | 10228 | 17534 | 39451 | 83285 |
| Power Required To Separate $H_2S$, MWt | 0 | 702 | 1579 | 2707 | 4211 | 6317 | 9475 | 14739 | 25267 | 56850 | 120016 |
| Power to Compress Natural Gas to 6.9 MPa (1,000 psig), MWt | 73 | 73 | 73 | 73 | 73 | 73 | 73 | 73 | 73 | 73 | 73 |
| Liquefaction Power Required To Make LNG, MWt | 660 | 660 | 660 | 660 | 660 | 660 | 660 | 660 | 660 | 660 | 660 |
| Supplemental Power Required, MWt | 733 | 948 | 1216 | 1561 | 2022 | 2666 | 3633 | 5244 | 8466 | 18132 | 37464 |
| Methane for Supplemental Power, mT/h | 53 | 68 | 88 | 113 | 146 | 193 | 262 | 379 | 612 | 1310 | 2707 |
| Carbon Dioxide Emitted, mT/h | 146 | 188 | 242 | 310 | 402 | 530 | 722 | 1042 | 1682 | 3602 | 7443 |

By comparing the data in Examples 1 to 11 to the data in Comparative Examples 12 to 22, it is shown that the use of hydrogen sulfide as fuel to power the separation of the feed gas stream into a hydrogen sulfide stream and a hydrocarbon gas stream and to process the hydrocarbon gas stream to form LNG yields more thermal power than is required by those process steps and permits production of electrical power for export as electricity. Conventional processes for producing LNG from feed gas streams containing significant amounts of hydrogen sulfide that utilize the Claus process to produce elemental sulfur from hydrogen sulfide, however, require supplemental combustion of methane and associated emission of carbon dioxide to meet the overall thermal and/or mechanical and/or electrical power requirements for the production of LNG.

Examples 23 to 33

In a process model using process steps in accordance with a process of the present invention, power calculations for the production of 1142 metric tons per hour of liquid natural gas (LNG) per hour from selected feed gas streams containing from 0% to 63% by volume of hydrogen sulfide, from 0% to 32% by volume carbon dioxide, and from 100% to 5% by volume methane and having a pressure of 1.7 MPa (250 psig) were performed using energy consumption data obtained from known refinery processes. In the process model, the feed gas stream was treated to separate water and liquid hydrocarbons from the feed gas stream. Next, hydrogen sulfide and carbon dioxide were removed from the feed gas stream using an amine extraction system to produce a hydrocarbon gas stream containing the methane. In the process model, the thermal power required to regenerate hydrogen sulfide and carbon dioxide from the hydrogen sulfide/carbon dioxide-loaded amine system was supplied as steam produced in a boiler. The boiler was assumed to have 100% thermal efficiency. In the process model, the thermal energy for the boiler was produced by combusting the entire recovered hydrogen sulfide stream with an oxidant containing molecular oxygen, wherein the molar ratio of the molecular oxygen to the hydrogen sulfide in the combustion was 1.5:1. The lower heating value of 6545 Btu per pound (15213 kilojoule per kilogram) of hydrogen sulfide was used in the calculations. A heating value for the regeneration of the hydrogen sulfide/carbon dioxide-loaded amine extraction solution of 4030 Btu per pound (9374 kilojoule per kilogram) of hydrogen sulfide produced was used in the calculations. A heating value for the regeneration of the hydrogen sulfide/carbon dioxide-loaded amine extraction solution of 1569 Btu per pound (3650 kilojoule per kilogram) of carbon dioxide, as described by Lars Erik Øi, in, "Aspen HYSYS Simulation of $CO_2$ Removal by Amine Absorption from a Gas Based Power Plant" SIMS2007 Conference, Gøteborg, Sweden, Oct. 30 and 31, 2007, was used in the calculations. The power requirement for carbon dioxide compression, liquefaction, and pumping was estimated to be 0.11 MW per mT/h, as described by Baldwin et al. in "Capturing $CO_2$: Gas Compression vs. Liquefaction," Power, June 2009, electronic publication. In the process model, if supplemental power was necessary methane was used as fuel. The consumption of methane was estimated using the lower heating value of 21433 Btu per pound (49820 kilojoule per kilogram) of methane.

In the process model, the hydrocarbon gas stream containing methane produced by separation of hydrogen sulfide and carbon dioxide from the feed gas stream is processed to produce LNG. Power intensive steps included in the process model for processing the hydrocarbon gas stream to form the LNG were 1) compressing the hydrocarbon gas stream having a pressure of 1.7 MPa to form a compressed natural gas having a pressure of 6.9 MPa; and 2) liquefying the compressed natural gas to form LNG. Other steps included in forming LNG such as separating heavier hydrocarbons from the hydrocarbon gas stream, removing metals from the hydrocarbon gas stream, dehydrating the hydrocarbon gas stream, and separating non-hydrocarbon gases from the hydrocarbon gas stream were excluded from the process model from an energy/power perspective since the power required to effect these steps is very small relative to the power required to effect the steps of separating/regenerating hydrogen sulfide and carbon dioxide using an amine system, compressing the hydrocarbon gas stream to form a compressed natural gas, and liquefying the compressed natural gas. In the process model, the thermal power required to compress and liquefy the hydrocarbon gas stream was provided from the boiler in which the hydrogen sulfide was combusted. If supplemental power is required to produce the LNG the thermal power was provided from combustion of methane produced by the process.

TABLE 3 lists power data, LNG production data, sulfur dioxide production data, and carbon dioxide emission data for the production of LNG from the selected feed gas streams using hydrogen sulfide as a source of power.

TABLE 3

| Illustrative Example No. | 23 | 24 | 25 | 26 | 27 | 28 | 29 | 30 | 31 | 32 | 33 |
|---|---|---|---|---|---|---|---|---|---|---|---|
| Volume %, $H_2S$ | 0 | 6.6 | 13.2 | 19.8 | 26.4 | 33 | 39.6 | 46.2 | 52.8 | 59.4 | 62.7 |
| Volume %, $CO_2$ | 0 | 3.4 | 6.8 | 10.2 | 13.6 | 17 | 20.4 | 23.8 | 27.2 | 30.6 | 32.3 |
| Volume %, $CH_4$ | 100 | 90 | 80 | 70 | 60 | 50 | 40 | 30 | 20 | 10 | 5 |
| LNG Produced, mT/h | 1142 | 1142 | 1142 | 1142 | 1142 | 1142 | 1142 | 1142 | 1142 | 1142 | 1142 |
| Sulfur Dioxide Produced, mT/h | 0 | 335 | 753 | 1292 | 2009 | 3014 | 4521 | 7032 | 12055 | 27123 | 57260 |
| Carbon Dioxide Produced, mT/h | 0 | 119 | 267 | 457 | 712 | 1067 | 1601 | 2490 | 4269 | 9606 | 20280 |
| Power Generated by $H_2S$ Burning, MWt | 0 | 752 | 1692 | 2900 | 4511 | 6767 | 10151 | 15790 | 27068 | 60903 | 128574 |
| Power Required To Separate $H_2S$ and $CO_2$, MWt | 0 | 583 | 1313 | 2250 | 3500 | 5250 | 7876 | 12251 | 21002 | 47254 | 99759 |
| Excess Power After Purifying Natural Gas, MWt | 0 | 169 | 379 | 650 | 1011 | 1517 | 2275 | 3539 | 6066 | 13649 | 28815 |
| Power to Compress Natural Gas to 6.9 MPa (1,000 psig), MWt | 73 | 73 | 73 | 73 | 73 | 73 | 73 | 73 | 73 | 73 | 73 |
| Liquefaction Power Required To Make LNG, MWt | 660 | 660 | 660 | 660 | 660 | 660 | 660 | 660 | 660 | 660 | 660 |
| Excess Power After Making LNG, MWt | 0 | 0 | 0 | 0 | 278 | 784 | 1542 | 2806 | 5333 | 12916 | 28082 |
| Power Required To Liquefy $CO_2$, MWt | 0 | 13 | 29 | 50 | 78 | 117 | 176 | 274 | 470 | 1057 | 2231 |
| Excess Power After Making LNG and $CO_2$(l), MWt | 0 | 0 | 0 | 0 | 200 | 667 | 1366 | 2532 | 4863 | 11859 | 25851 |
| Supplemental Power Required, MWt | 733 | 577 | 383 | 133 | 0 | 0 | 0 | 0 | 0 | 0 | 0 |
| Methane Required For Supplemental Power, mT/h | 53 | 42 | 28 | 10 | 0 | 0 | 0 | 0 | 0 | 0 | 0 |
| Power Export at 40% Efficiency After Making LNG & $CO_2$(L), MWe | 0 | 0 | 0 | 0 | 80 | 267 | 546 | 1013 | 1946 | 4744 | 10341 |
| Power Export at 60% Efficiency, After Making LNG & $CO_2$(L), MWe | 0 | 0 | 0 | 0 | 120 | 400 | 820 | 1519 | 2918 | 7116 | 15511 |
| Power Export After Making LNG & $CO_2$(L), kWh/Kg $H_2S$ | 0 | 0 | 0 | 0 | 0.2 | 0.4 | 0.6 | 0.7 | 0.8 | 0.8 | 0.8 |
| Carbon Dioxide Emitted, mT/h | 146 | 115 | 76 | 26 | 0 | 0 | 0 | 0 | 0 | 0 | 0 |
| Carbon Dioxide Captured, % | 0 | 51 | 78 | 95 | >95 | >95 | >95 | >95 | >95 | >95 | >95 |

Using the values in TABLE 3, the maximum amount of thermal power available upon separation of hydrogen sulfide and carbon dioxide from the selected feed gas streams and combustion of the separated hydrogen sulfide (basis production of 1142 metric tons of LNG per hour from the feed gas streams) was calculated to be 169 MWt at 90% methane, 6.6% $H_2S$, and 3.4% $CO_2$; 379 MWt at 80%, 13.2%, and 6.8% $CH_4$, $H_2S$, and $CO_2$ respectively; 650 MWt at 70%, 19.8%, and 10.2% $CH_4$, $H_2S$, and $CO_2$ respectively; 1011 MWt at 60%, 26.4%, and 13.6% $CH_4$, $H_2S$, and $CO_2$ respectively; 1517 MWt at 50%, 33%, and 17% $CH_4$, $H_2S$, and $CO_2$ respectively; 2275 MWt at 40%, 39.6%, and 20.4% $CH_4$, $H_2S$, and $CO_2$ respectively; 3539 MWt at 30%, 46.2%, and 20.4% $CH_4$, $H_2S$, and $CO_2$ respectively; 6066 MWt at 20%, 52.8%, and 27.2% $CH_4$, $H_2S$, and $CO_2$ respectively; 13649 MWt at 10%, 59.4%, and 30.6% $CH_4$, $H_2S$, and $CO_2$ respectively; and 28815 MWt at 5%, 62.7%, and 32.3% $CH_4$, $H_2S$, and $CO_2$ respectively [available thermal power=(power generated by combusting $H_2S$) minus (power consumed by separating hydrogen sulfide and carbon dioxide from feed gas stream)]. The amount of excess thermal power generated by combusting hydrogen sulfide separated from the selected feed gas streams and providing a portion of the thermal power produced thereby sufficient to separate the hydrogen sulfide and carbon dioxide from the feed gas stream to produce a methane-containing hydrocarbon gas stream and to process the hydrocarbon gas stream to produce liquefied natural gas (basis production of 1142 metric tons of LNG per hour) was calculated to be 278 MWt at 60%, 26.4%, and 13.6% $CH_4$, $H_2S$, and $CO_2$ respectively; 784 MWt at 50%, 33%, and 17% $CH_4$, $H_2S$, and $CO_2$ respectively; 1542 MWt at 40%, 39.6%, and 20.4% $CH_4$, $H_2S$, and $CO_2$ respectively; 2806 MWt at 30%, 46.2%, and 20.4% $CH_4$, $H_2S$, and $CO_2$ respectively; 5333 MWt at 20%, 52.8%, and 27.2% $CH_4$, $H_2S$, and $CO_2$ respectively; 12916 MWt at 10%, 59.4%, and 30.6% $CH_4$, $H_2S$, and $CO_2$ respectively; and 28082 MWt at 5%, 62.7%, and 32.3% $CH_4$, $H_2S$, and $CO_2$ respectively [excess thermal power=(thermal power generated from combustion of separated hydrogen sulfide) minus (thermal power consumed to separate hydrogen sulfide, carbon dioxide, and hydrocarbon gas stream from the feed gas stream plus thermal power consumed to compress the separated hydrocarbon gas stream plus thermal power consumed to liquefy the compressed hydrocarbon gas stream to produce LNG)]. The amount of excess thermal power generated by combustion of hydrogen sulfide from the selected feed gas streams and providing a portion of the thermal power produced thereby sufficient to separate the hydrogen sulfide, carbon dioxide, and a methane-containing hydrocarbon gas stream from the feed gas stream, and to liquefy the separated carbon dioxide, and to process the hydrocarbon gas stream to produce liquefied natural gas (basis production of 1142 metric tons of LNG per hour) was calculated to be 200 MWt at 60%, 26.4%, and 13.6% $CH_4$, $H_2S$, and $CO_2$ respectively; 667 MWt at %, 33%, and 17% $CH_4$, $H_2S$, and $CO_2$ respectively; 1366 MWt at 40%, 39.6%, and 20.4% $CH_4$, $H_2S$, and $CO_2$ respectively; 2532 MWt at 30%, 46.2%, and 20.4% $CH_4$, $H_2S$, and $CO_2$ respectively; 4863 MWt at 20%, 52.8%, and 27.2% $CH_4$, $H_2S$, and $CO_2$ respectively; 11859 MWt at 10%, 59.4%, and 30.6% $CH_4$, $H_2S$, and $CO_2$ respectively; and 25851 MWt at 5%, 62.7%, and 32.3% $CH_4$, $H_2S$, and $CO_2$ respectively [excess thermal power=(thermal power generated from combustion of separated hydrogen sulfide) minus (thermal power consumed to separate hydrogen sulfide, carbon dioxide, and hydrocarbon gas stream from the feed gas stream plus thermal power consumed to compress the separated hydrocarbon gas stream plus thermal power consumed to liquefy the compressed hydrocarbon gas stream to produce LNG plus thermal power consumed to liquefy $CO_2$)].

The data in Examples 23 to 33 demonstrate that capturing all the thermal power from combustion of a hydrogen sulfide stream that is produced from a feed gas stream containing hydrogen sulfide and carbon dioxide with the balance being hydrocarbons may generate most or all of the power required for separating the feed gas stream into the hydrogen sulfide stream, a hydrocarbon gas stream, and a carbon dioxide stream and also produce sufficient power for processing the hydrocarbon gas stream to produce LNG and for processing the carbon dioxide stream to produce liquid carbon dioxide. Significant power for export may be generated as the volume of hydrogen sulfide in the feed gas stream exceeds about 25 volume %.

Comparative Examples 34 to 44

In a process model using process steps in accordance with the production of LNG using a conventional Claus process, power calculations for the production of 1142 metric tons of LNG per hour from selected feed gas streams containing from 0% to 63% by volume of hydrogen sulfide, from 0% to 32% by volume carbon dioxide, and from 100% to 5% by volume methane and having a pressure of 1.7 MPa (250 psig) were performed using energy consumption data obtained from known refinery process. In the process model, the feed gas stream was treated to separate water and liquid hydrocarbons from the feed gas stream. Next, hydrogen sulfide and carbon dioxide were removed from the feed gas stream using an amine extraction system to produce a methane-containing hydrocarbon gas stream. In the process model, the thermal power required to regenerate hydrogen sulfide from the hydrogen sulfide/carbon dioxide-loaded amine system was supplied as steam produced from Claus Process heat recovery unit(s) and operation of a supplemental boiler that was fueled by natural gas produced in the process. The boiler was assumed to have 100% thermal efficiency. In the process model, hydrogen sulfide produced from regeneration of the amine system was converted to elemental sulfur via the Claus Process. A heating value of 2973 Btu per pound (6915 kilojoule per kilogram) of elemental sulfur produced from the Claus Process was used in the calculations. A heating value for the regeneration of the hydrogen sulfide loaded amine extraction solution of 4030 Btu per pound (9374 kilojoule per kilogram) of hydrogen sulfide produced was used in the calculations. A heating value for the regeneration of the carbon dioxide loaded amine extraction solution of 1569 Btu per pound (3650 kilojoule per kilogram) of carbon dioxide was used in the calculations. A power requirement for carbon dioxide compression, liquefaction, and pumping of 0.11 MW per mT/h was used in the calculations. In the process model, if supplemental power was necessary methane was used as fuel. The consumption of methane was estimated using the lower heating value of 21433 Btu per pound (49820 kilojoule per kilogram) of methane.

In the process model, the hydrocarbon gas stream produced by separation of the hydrogen sulfide and carbon dioxide from the feed gas stream is processed to produce LNG. Power intensive steps included in the process model for processing the hydrocarbon gas stream to form the LNG were 1) compressing the hydrocarbon gas stream having a pressure of 1.7 MPa to form a compressed natural gas having a pressure of 6.9 MPa; and 2) liquefying the compressed natural gas to form LNG. Other steps included in forming LNG such as separating heavier hydrocarbons from the hydrocarbon gas stream, removing metals from the hydrocarbon gas stream, dehydrating the hydrocarbon gas stream, and separating non-hydrocarbon gases from the hydrocarbon gas stream were excluded from the process model from an energy/power perspective since the power required to effect these steps is very small relative to the power required to effect the steps of separating/regenerating hydrogen sulfide using an amine system, compressing the hydrocarbon gas stream to form a compressed natural gas, and liquefying the compressed natural gas to form LNG. In the process model, the thermal power required to compress and liquefy the hydrocarbon gas stream was provided from the Claus process heat recovery unit(s) and, if necessary, the supplemental boiler in which methane produced by the process was burned.

TABLE 4 lists power data, LNG production data, elemental sulfur data, and carbon dioxide emission data for the production of LNG from the selected feed gas streams utilizing the Claus process. As shown in TABLE 4, the amount of carbon dioxide emission increases significantly as the amount of methane required for supplemental power is increased for feed gas streams that contain higher quantities of hydrogen sulfide and carbon dioxide, and lesser quantities of methane.

TABLE 4

| Comparative Example No. | 34 | 35 | 36 | 37 | 38 | 39 | 40 | 41 | 42 | 43 | 44 |
|---|---|---|---|---|---|---|---|---|---|---|---|
| Volume %, $H_2S$ | 0 | 6.6 | 13.2 | 19.8 | 26.4 | 33 | 39.6 | 46.2 | 52.8 | 59.4 | 62.7 |
| Volume %, $CO_2$ | 0 | 3.4 | 6.8 | 10.2 | 13.6 | 17 | 20.4 | 23.8 | 27.2 | 30.6 | 32.3 |
| Volume %, $CH_4$ | 100 | 90 | 80 | 70 | 60 | 50 | 40 | 30 | 20 | 10 | 5 |
| LNG Produced, mT/h | 1142 | 1142 | 1142 | 1142 | 1142 | 1142 | 1142 | 1142 | 1142 | 1142 | 1142 |
| Elemental Sulfur Produced, mT/h | 0 | 167 | 377 | 646 | 1005 | 1507 | 2260 | 3516 | 6027 | 13562 | 28630 |
| Power Generated by Claus Plant, MWt | 0 | 321 | 723 | 1240 | 1929 | 2893 | 4340 | 6750 | 11572 | 26037 | 54968 |
| Power Required To Separate $H_2S$ and $CO_2$, MWt | 0 | 583 | 1313 | 2250 | 3500 | 5250 | 7876 | 12251 | 21002 | 47254 | 99759 |
| Power to Compress Natural Gas to 6.9 MPa (1,000 psig), MWt | 73 | 73 | 73 | 73 | 73 | 73 | 73 | 73 | 73 | 73 | 73 |
| Liquefaction Power Required To Make LNG, MWt | 660 | 660 | 660 | 660 | 660 | 660 | 660 | 660 | 660 | 660 | 660 |
| Supplemental Power Required, MWt | 733 | 995 | 1322 | 1743 | 2304 | 3090 | 4269 | 6233 | 10162 | 21950 | 45524 |
| Methane Required for Supplemental Power, mT/h | 53 | 72 | 96 | 126 | 166 | 223 | 308 | 450 | 734 | 1586 | 3289 |
| Total Carbon Dioxide Emitted, mT/h | 146 | 316 | 530 | 804 | 1169 | 1681 | 2449 | 3729 | 6288 | 13967 | 29324 |

By comparing the data in Examples 23 to 33 to the data in Comparative Examples 34 to 44, it is shown that the use of hydrogen sulfide as fuel to power the separation of hydrogen sulfide and carbon dioxide from a feed gas stream to produce natural gas and the subsequent liquefaction of the natural gas to LNG and the subsequent liquefaction of the carbon dioxide yields most, and typically all, of the power required by those processes and may permit production of power for export. Conventional processes for producing LNG from streams containing significant amounts of hydrogen sulfide and carbon dioxide that utilize the Claus process to form elemental sulfur from hydrogen sulfide, however, require supplemental combustion of methane and associated emissions of carbon dioxide to meet the overall energy requirements of the process.

Examples 45 to 55

In a process model using process steps in accordance with a process of the present invention, power calculations for the production of 1142 metric tons of compressed natural gas per hour (compressed to a pressure of 24.1 MPa (3500 psig)) from selected feed gas streams containing methane and from 5% to 95% by volume hydrogen sulfide and having a pressure of 1.7 MPa (250 psig) were performed using energy consumption data obtained from known refinery processes. In the process model, a selected feed gas stream was treated to separate water and liquid hydrocarbons from the feed gas stream. Next, hydrogen sulfide was removed from the feed gas stream using an amine extraction system to produce a methane-containing hydrocarbon gas stream. The power required to regenerate the hydrogen sulfide from the hydrogen sulfide-loaded amine system was supplied as steam produced in a boiler. The boiler was assumed to have 100% thermal efficiency. In the process model, the thermal power for the boiler was produced by combusting the entire recovered hydrogen sulfide stream with an oxidant containing molecular oxygen, wherein the molar ratio of the molecular oxygen to the hydrogen sulfide in the combustion was 1.5:1. The lower heating value of 6545 Btu per pound (15213 kilojoule per kilogram) of hydrogen sulfide was used in the calculations. A heating value for the regeneration of the hydrogen sulfide loaded amine extraction solution of 4030 Btu per pound (9374 kilojoule per kilogram) of hydrogen sulfide produced was used in the calculations. In the process model, if supplemental power was necessary, methane was used as fuel. In the calculations, the consumption of methane was estimated using the lower heating value of 21433 Btu per pound (49820 kilojoule per kilogram) of methane.

In the process model, the methane-containing hydrocarbon gas stream produced by separation of hydrogen sulfide from the feed gas stream is processed to produce compressed natural gas (CNG). The power intensive step included in the process model for processing the hydrocarbon gas stream to form the CNG was compressing the hydrocarbon gas stream to a pressure of 24.1 MPa to form the CNG. Other steps included in forming CNG such as separating heavier hydrocarbons from the hydrocarbon gas stream, removing metals from the hydrocarbon gas stream, dehydrating the hydrocarbon gas stream, and separating non-hydrocarbon gases from the hydrocarbon gas stream were excluded from the process model from an energy/power perspective since the power required to effect these steps is very small relative to the power required to effect the steps of separating/regenerating hydrogen sulfide using an amine system and compressing the hydrocarbon gas stream to form the CNG. In the process model, the thermal power required to compress the hydrocarbon gas stream was provided from the boiler in which the hydrogen sulfide was combusted.

TABLE 5 lists power data, CNG production data, sulfur dioxide production data, and carbon dioxide emission data from selected feed gas streams containing methane and from 5% to 95% by volume hydrogen sulfide. Using the values in TABLE 5, the amount of excess thermal power generated by combusting hydrogen sulfide from a selected feed gas stream to produce a methane-containing hydrocarbon gas stream and to process the hydrocarbon gas stream to produce CNG (basis production of 1142 metric tons of CNG per hour at 24.1 MPa from a feed gas stream having a pressure of 1.7 MPa) was calculated to be 121 MWt at 10% $H_2S$, 668 MWt at 20% $H_2S$, 1371 MWt at 30% $H_2S$, 2308 MWt at 40% $H_2S$, 3620 MWt at 50% $H_2S$, 5589 MWt at 60% $H_2S$, 8869 MWt at 70% $H_2S$, 15430 MWt at 80% $H_2S$, 35112 MWt at 90% $H_2S$, and 74477 MWt at 95% $H_2S$ [excess thermal power=(thermal power generated from combustion of separated hydrogen sulfide) minus (thermal power consumed to separate hydrogen sulfide and the hydrocarbon gas stream from the feed gas stream plus thermal power consumed to compress the separated hydrocarbon gas stream to produce CNG)].

The data in Examples 45 to 55 demonstrate generation of thermal power from combustion of a hydrogen sulfide stream with an oxidant at a molar ratio of molecular oxygen to hydrogen sulfide of 1.5:1, where the hydrogen sulfide stream is separated from a feed gas stream containing hydrocarbons and at least 10 vol. % hydrogen sulfide, where a hydrocarbon gas stream is also separated from the feed gas stream and the hydrocarbon gas stream is processed to produce compressed natural gas, and where the thermal power is utilized in the steps of separating the feed gas stream into the hydrogen sulfide stream and the hydrocarbon gas stream and processing the hydrocarbon gas stream to produce compressed natural gas.

The data in Examples 45 to 55 also demonstrate generation of thermal power from combustion of more than one third of a hydrogen sulfide stream with an oxidant at a molar ratio of molecular oxygen to hydrogen sulfide of 1.5 to 1, where the hydrogen sulfide stream is separated from a feed gas stream containing hydrocarbons and at least 5 vol. % hydrogen sulfide, where a hydrocarbon gas stream is also separated from the feed gas stream and the hydrocarbon gas stream is processed to produce compressed natural gas.

Furthermore, the data in Examples 45 to 55 demonstrates that the process of the present invention utilizing a feed gas stream containing hydrocarbons and at least 10 vol. % hydrogen sulfide generates over 1100 $MW_t$ of thermal power, of which over 120 $MW_t$ of thermal power is generated in excess of the power required to separate the feed gas stream into a hydrocarbon gas stream and a hydrogen sulfide stream and to process the hydrocarbon gas stream to produce compressed natural gas. Upon conversion of the excess thermal power to electrical power, at least 49 megawatts of electric power is available for export as electricity at a 40% efficiency while at most 0.1 grams of carbon dioxide per gram of hydrocarbons in the feed gas stream are produced during combustion of the hydrogen sulfide.

hydrocarbon gas stream. In the process model, the thermal power required to regenerate hydrogen sulfide from the hydrogen sulfide loaded-amine system was supplied as steam produced from Claus Process heat recovery unit(s) and operation of a supplemental boiler that was fueled by natural gas produced in the process. The boiler was assumed to have 100% thermal efficiency. In the process model, hydrogen sulfide produced from regeneration of the amine system was converted to elemental sulfur via the Claus Process. A heating value of 2973 Btu per pound (6915 kilojoule per kilogram) of elemental sulfur produced from the Claus Process was used in the calculations. A heating value for the regeneration of the hydrogen sulfide loaded amine extraction solution of 4030 Btu per pound (9374 kilojoule per kilogram) of hydrogen sulfide produced was used in the calculations. In the process model, methane was used as fuel for generating supplemental power. The consumption of methane was estimated using the lower heating value of 21433 Btu per pound (49820 kilojoule per kilogram) of methane.

In the process model, the methane-containing hydrocarbon gas stream produced by separation of hydrogen sulfide from the feed gas stream is processed to produce compressed natural gas (CNG). The power intensive step included in the process model for processing the hydrocarbon gas stream to form the CNG was compressing the hydrocarbon gas stream to a pressure of 24.1 MPa to form the CNG. Other steps included in forming CNG such as separating heavier hydrocarbons from the hydrocarbon gas stream, removing metals from the hydrocarbon gas stream, dehydrating the hydrocarbon gas stream, and separating non-hydrocarbon gases from

TABLE 5

| Illustrative Example No. | 45 | 46 | 47 | 48 | 49 | 50 | 51 | 52 | 53 | 54 | 55 |
|---|---|---|---|---|---|---|---|---|---|---|---|
| Volume %, $H_2S$ | 5 | 10 | 20 | 30 | 40 | 50 | 60 | 70 | 80 | 90 | 95 |
| Volume %, $CH_4$ | 95 | 90 | 80 | 70 | 60 | 50 | 40 | 30 | 20 | 10 | 5 |
| CNG Produced, mT/h | 1142 | 1142 | 1142 | 1142 | 1142 | 1142 | 1142 | 1142 | 1142 | 1142 | 1142 |
| Sulfur Dioxide Produced, mT/h | 240 | 507 | 1142 | 1957 | 3044 | 4566 | 6849 | 10654 | 18265 | 41096 | 86758 |
| Power Generated By $H_2S$ Burning, MWt | 540 | 1139 | 2563 | 4394 | 6835 | 10253 | 15380 | 23924 | 41012 | 92278 | 194809 |
| Power Required To Separate $H_2S$, MWt | 332 | 702 | 1579 | 2707 | 4211 | 6317 | 9475 | 14739 | 25267 | 56850 | 120016 |
| Excess Power After Purifying Natural Gas, MWt | 207 | 437 | 984 | 1687 | 2624 | 3936 | 5905 | 9185 | 15746 | 35428 | 74793 |
| Power Required To Make CNG, MWt | 316 | 316 | 316 | 316 | 316 | 316 | 316 | 316 | 316 | 316 | 316 |
| Excess Power Produced After Making CNG, MWt | 0 | 121 | 668 | 1371 | 2308 | 3620 | 5589 | 8869 | 15430 | 35112 | 74477 |
| Power Export at 40% Efficiency After Making CNG, MWe | 0 | 49 | 267 | 548 | 923 | 1448 | 2235 | 3548 | 6172 | 14045 | 29791 |
| Power Export at 60% Efficiency After Making CNG, MWe | 0 | 73 | 401 | 823 | 1385 | 2172 | 3353 | 5321 | 9258 | 21067 | 44686 |
| Power Exported After Making CNG, kWh/kg $H_2S$ | 0 | 0.4 | 1.1 | 1.3 | 1.4 | 1.5 | 1.5 | 1.6 | 1.6 | 1.6 | 1.6 |
| Supplemental Power Required, MWt | 109 | 0 | 0 | 0 | 0 | 0 | 0 | 0 | 0 | 0 | 0 |
| Methane Required for Supplemental Power, mT/h | 8 | 0 | 0 | 0 | 0 | 0 | 0 | 0 | 0 | 0 | 0 |
| Carbon Dioxide Emitted, mT/h | 22 | 0 | 0 | 0 | 0 | 0 | 0 | 0 | 0 | 0 | 0 |

Comparative Examples 56 to 66

In a process model using process steps in accordance with the production of CNG using a conventional Claus process, power calculations for the production of 1142 metric tons of CNG per hour at a pressure of 24.1 MPa (3500 psig) from selected feed gas streams containing methane and from 5% to 95% hydrogen sulfide and having a pressure of 1.7 MPa (250 psig) were performed using energy consumption data obtained from a known refinery process. In the process model, the feed gas stream was treated to separate water and liquid hydrocarbons from the feed gas stream. Next, hydrogen sulfide was removed from the feed gas stream using an amine extraction system to produce a methane-containing hydrocarbon gas stream were excluded from the process model from an energy/power perspective since the power required to effect these steps is very small relative to the power required to effect the steps of separating/regenerating hydrogen sulfide using an amine system and compressing the hydrocarbon gas stream to form the CNG. In the process model, the thermal power required to compress the hydrocarbon gas stream to form the CNG was provided from the Claus process heat recovery unit(s) and, if necessary, the supplemental boiler in which methane produced by the process was burned.

TABLE 6 lists power data, CNG production data, elemental sulfur production data, and carbon dioxide emission data for the production of CNG from the selected feed gas streams containing methane and from 0% to 95% by volume hydrogen sulfide utilizing the conventional Claus process. As shown in TABLE 6, the amount of methane fuel required for supplemental power for hydrogen sulfide separation and to produce CNG increases significantly as the amount of hydrogen sulfide in the feed stream increases. By comparing the data in Examples 45 to 55 to the data in Comparative Examples 56 to 66, it is shown that the use of hydrogen sulfide as fuel to power the separation of the feed gas stream into a hydrogen sulfide stream and a hydrocarbon gas stream and to process the hydrocarbon gas stream to form CNG typically yields more thermal power than is required by those process steps and permits production of electrical power for export as electricity. Conventional processes for producing CNG from feed gas streams containing significant amounts of hydrogen sulfide that utilize the Claus process to produce elemental sulfur from hydrogen sulfide, however, typically require supplemental combustion of methane and associated emission of carbon dioxide to meet the overall thermal and/or mechanical power requirements for the production of CNG.

regeneration of the carbon dioxide-loaded amine extraction solution of 1569 Btu per pound (3650 kilojoule per kilogram) of carbon dioxide, as described by Lars Erik Øi, in, "Aspen HYSYS Simulation of $CO_2$ Removal by Amine Absorption from a Gas Based Power Plant" SIMS2007 Conference, Gøteborg, Sweden, Oct. 30 and 31, 2007, was used in the calculations. The power requirement for carbon dioxide compression, liquefaction, and pumping was estimated to be 0.11 MW per mT/h, as described by Baldwin et al. in "Capturing $CO_2$: Gas Compression vs. Liquefaction," Power, June 2009, electronic publication. In the process model, if supplemental power was necessary methane was used as fuel. The consumption of methane was estimated using the lower heating value of 21433 Btu per pound (49820 kilojoule per kilogram) of methane.

In the process model, the methane-containing hydrocarbon gas stream produced by separation of hydrogen sulfide and carbon dioxide from the feed gas stream is processed to produce compressed natural gas (CNG). The power intensive step included in the process model for processing the hydro-

TABLE 6

| Comparative Example No. | 56 | 57 | 58 | 59 | 60 | 61 | 62 | 63 | 64 | 65 | 66 |
|---|---|---|---|---|---|---|---|---|---|---|---|
| Volume %, $H_2S$ | 0 | 10 | 20 | 30 | 40 | 50 | 60 | 70 | 80 | 90 | 95 |
| Volume %, $CH_4$ | 100 | 90 | 80 | 70 | 60 | 50 | 40 | 30 | 20 | 10 | 5 |
| CNG Produced, mT/h | 1142 | 1142 | 1142 | 1142 | 1142 | 1142 | 1142 | 1142 | 1142 | 1142 | 1142 |
| Elemental Sulfur Produced, mT/h | 0 | 254 | 571 | 978 | 1522 | 2283 | 3425 | 5327 | 9132 | 20548 | 43379 |
| Power Generated By Claus Plant, MWt | 0 | 487 | 1096 | 1879 | 2922 | 4383 | 6575 | 10228 | 17534 | 39451 | 83285 |
| Power Required To Separate $H_2S$, MWt | 0 | 702 | 1579 | 2707 | 4211 | 6317 | 9475 | 14739 | 25267 | 56850 | 120016 |
| Power Required To Make CNG, MWt | 316 | 316 | 316 | 316 | 316 | 316 | 316 | 316 | 316 | 316 | 316 |
| Supplemental Power Required, MWt | 316 | 531 | 799 | 1145 | 1605 | 2249 | 3216 | 4827 | 8049 | 17715 | 37047 |
| Methane for Supplemental Power, mT/h | 23 | 38 | 58 | 83 | 116 | 163 | 232 | 349 | 582 | 1280 | 2677 |
| Carbon Dioxide Emitted, mT/h | 63 | 105 | 159 | 227 | 319 | 447 | 639 | 959 | 1599 | 3520 | 7361 |

Examples 67 to 77

In a process model using process steps in accordance with a process of the present invention, power calculations for the production of 1142 metric tons of compressed natural gas per hour (compressed to a pressure of 24.1 MPa (3500 psig)) to produce CNG from selected feed streams containing from 0% to 63% by volume of hydrogen sulfide, from 0% to 32% by volume carbon dioxide, and from 100% to 5% by volume methane and having a pressure of 1.7 MPa (250 psig) were performed using energy consumption data obtained from known refinery processes. In the process model, the selected feed gas stream was treated to separate water and liquid hydrocarbons from the feed gas stream. Next, hydrogen sulfide and carbon dioxide were removed from the feed gas stream using an amine extraction system to produce a methane-containing hydrocarbon gas stream. In the process model, the thermal power required to regenerate hydrogen sulfide and carbon dioxide from the hydrogen sulfide/carbon dioxide-loaded amine system was supplied as steam produced in a boiler. The boiler was assumed to have 100% thermal efficiency. In the process model, the thermal energy for the boiler was produced by combusting the entire recovered hydrogen sulfide stream with an oxidant containing molecular oxygen, wherein the molar ratio of the molecular oxygen to the hydrogen sulfide in the combustion was 1.5:1. The lower heating value of 6545 Btu per pound (15213 kilojoule per kilogram) of hydrogen sulfide was used in the calculations. A heating value for the regeneration of the hydrogen sulfide-loaded amine extraction solution of 4030 Btu per pound (9374 kilojoule per kilogram) of hydrogen sulfide produced was used in the calculations. A heating value for the carbon gas stream to form the CNG was compressing the hydrocarbon gas stream to a pressure of 24.1 MPa to form the CNG. Other steps included in forming CNG such as separating heavier hydrocarbons from the hydrocarbon gas stream, removing metals from the hydrocarbon gas stream, dehydrating the hydrocarbon gas stream, and separating non-hydrocarbon gases from the hydrocarbon gas stream were excluded from the process model from an energy/power perspective since the power required to effect these steps is very small relative to the power required to effect the steps of separating/regenerating hydrogen sulfide and carbon dioxide using an amine system, compressing the hydrocarbon gas stream to form the CNG, and compressing carbon dioxide to form liquid carbon dioxide. In the process model, the thermal power required to compress the hydrocarbon gas stream and to compress carbon dioxide was provided from the boiler in which the hydrogen sulfide was combusted.

TABLE 7 lists power data, CNG production data, sulfur dioxide production data, and carbon dioxide emission data for the production of CNG from selected feed gas streams having compositions ranging from 0% to 63% by volume of hydrogen sulfide, from 0% to 32% by volume carbon dioxide, and from 100% to 5% by volume methane using hydrogen sulfide as a source of power. Using the values in TABLE 7 the amount of excess thermal power generated by combusting hydrogen sulfide separated from the selected feed gas streams and providing a portion of the thermal power produced thereby sufficient to separate the hydrogen sulfide and carbon dioxide from the feed gas stream to produce a hydrocarbon gas stream and to process the hydrocarbon gas stream to produce CNG (basis production of 1142 metric tons of CNG per hour at 24.1 MPa from a feed gas stream having a pressure of 1.7 MPa (250 psig)) was calculated to be 63 MWt at 80%, 13.2%, and 6.8% $CH_4$, $H_2S$, and $CO_2$ respectively; 334 MWt at 70%, 19.8%, and 10.2% $CH_4$, $H_2S$, and $CO_2$ respectively; 695 MWt at 60%, 26.4%, and 13.6% $CH_4$, $H_2S$, and $CO_2$ respectively; 1200 MWt at 50%, 33%, and 17% $CH_4$, $H_2S$, and $CO_2$ respectively; 1959 MWt at 40%, 39.6%, and 20.4% $CH_4$, $H_2S$, and $CO_2$ respectively; 3223 MWt at 30%, 46.2%, and 20.4% $CH_4$, $H_2S$, and $CO_2$ respectively; 5750 MWt at 20%, 52.8%, and 27.2% $CH_4$, $H_2S$, and $CO_2$ respectively; 13333 MWt at 10%, 59.4%, and 30.6% $CH_4$, $H_2S$, and $CO_2$ respectively; and 28499 MWt at 5%, 62.7%, and 32.3% $CH_4$, $H_2S$, and $CO_2$ respectively respectively [excess thermal power= (thermal power generated from combustion of separated hydrogen sulfide) minus (thermal power consumed to separate hydrogen sulfide, carbon dioxide, and the hydrocarbon gas stream from the feed gas stream plus thermal power consumed to compress the separated hydrocarbon gas stream to form CNG)]. The amount of excess thermal power generated by combustion of hydrogen sulfide from the selected feed gas streams and providing a portion of the thermal power produced thereby sufficient to separate the hydrogen sulfide, carbon dioxide, and methane-containing hydrocarbon gas stream from the feed gas stream, and to liquefy the separated carbon dioxide, and to process the hydrocarbon gas stream to produce CNG (basis production of 1142 metric tons of CNG per hour at 24.1 MPa from a feed gas stream at a pressure of 1.7 MPa) was calculated to be 34 MWt at 80%, 13.2%, and 6.8% $CH_4$, $H_2S$, and $CO_2$ respectively; 284 MWt at 70%, 19.8%, and 10.2% $CH_4$, $H_2S$, and $CO_2$ respectively; 617 MWt at 60%, 26.4%, and 13.6% $CH_4$, $H_2S$, and $CO_2$ respectively; 1083 MWt at 50%, 33%, and 17% $CH_4$, $H_2S$, and $CO_2$ respectively; 1783 MWt at 40%, 39.6%, and 20.4% $CH_4$, $H_2S$, and $CO_2$ respectively; 2949 MWt at 30%, 46.2%, and 20.4% $CH_4$, $H_2S$, and $CO_2$ respectively; 5281 MWt at 20%, 52.8%, and 27.2% $CH_4$, $H_2S$, and $CO_2$ respectively; 12276 MWt at 10%, 59.4%, and 30.6% $CH_4$, $H_2S$, and $CO_2$ respectively; and 26268 MWt at 5%, 62.7%, and 32.3% $CH_4$, $H_2S$, and $CO_2$ respectively [excess thermal power=(thermal power generated from combustion of separated hydrogen sulfide) minus (thermal power consumed to separate hydrogen sulfide, carbon dioxide, and hydrocarbon gas stream from the feed gas stream plus thermal power consumed to compress the separated hydrocarbon gas stream to form CNG plus thermal power consumed to liquefy $CO_2$)].

TABLE 7

| Illustrative Example No. | 67 | 68 | 69 | 70 | 71 | 72 | 73 | 74 | 75 | 76 | 77 |
|---|---|---|---|---|---|---|---|---|---|---|---|
| Volume %, $H_2S$ | 0 | 6.6 | 13.2 | 19.8 | 26.4 | 33 | 39.6 | 46.2 | 52.8 | 59.4 | 62.7 |
| Volume %, $CO_2$ | 0 | 3.4 | 6.8 | 10.2 | 13.6 | 17 | 20.4 | 23.8 | 27.2 | 30.6 | 32.3 |
| Volume %, $CH_4$ | 100 | 90 | 80 | 70 | 60 | 50 | 40 | 30 | 20 | 10 | 5 |
| CNG Produced, mT/h | 1142 | 1142 | 1142 | 1142 | 1142 | 1142 | 1142 | 1142 | 1142 | 1142 | 1142 |
| Sulfur Dioxide Produced, mT/h | 0 | 335 | 753 | 1292 | 2009 | 3014 | 4521 | 7032 | 12055 | 27123 | 57260 |
| Carbon Dioxide Produced, mT/h | 0 | 119 | 267 | 457 | 712 | 1067 | 1601 | 2490 | 4269 | 9606 | 20280 |
| Power Generated by $H_2S$ Burning, MWt | 0 | 752 | 1692 | 2900 | 4511 | 6767 | 10151 | 15790 | 27068 | 60903 | 128574 |
| Power Required To Separate $H_2S$ and $CO_2$, MWt | 0 | 583 | 1313 | 2250 | 3500 | 5250 | 7876 | 12251 | 21002 | 47254 | 99759 |
| Excess Power After Purifying Natural Gas, MWt | 0 | 169 | 379 | 650 | 1011 | 1517 | 2275 | 3539 | 6066 | 13649 | 28815 |
| Power Required To Make CNG, MWt | 316 | 316 | 316 | 316 | 316 | 316 | 316 | 316 | 316 | 316 | 316 |
| Excess Power After Making CNG, MWt | 0 | 0 | 63 | 334 | 695 | 1201 | 1959 | 3223 | 5750 | 13333 | 28499 |
| Power Required To Liquefy $CO_2$, MWt | 0 | 13 | 29 | 50 | 78 | 117 | 176 | 274 | 470 | 1057 | 2231 |
| Excess Power After Making CNG and $CO_2(l)$, MWt | 0 | 0 | 34 | 284 | 617 | 1083 | 1783 | 2949 | 5281 | 12276 | 26268 |
| Supplemental Power Required, MWt | 316 | 161 | 0 | 0 | 0 | 0 | 0 | 0 | 0 | 0 | 0 |
| Methane Required For Supplemental Power, mT/h | 23 | 12 | 0 | 0 | 0 | 0 | 0 | 0 | 0 | 0 | 0 |
| Power Export at 40% Efficiency After Making CNG & $CO_2(l)$, MWe | 0 | 0 | 13 | 113 | 247 | 433 | 713 | 1179 | 2112 | 4911 | 10507 |
| Power Export at 60% Efficiency, After Making CNG & $CO_2(l)$, MWe | 0 | 0 | 20 | 170 | 370 | 650 | 1070 | 1769 | 3168 | 7366 | 15761 |
| Power Export After Making CNG & $CO_2(l)$, kWh/Kg $H_2S$ | 0 | 0 | 0.1 | 0.4 | 0.6 | 0.7 | 0.7 | 0.8 | 0.8 | 0.9 | 0.9 |
| Carbon Dioxide Emitted, mT/h | 63 | 32 | 0 | 0 | 0 | 0 | 0 | 0 | 0 | 0 | 0 |
| Carbon Dioxide Captured, % | | 79 | >95 | >95 | >95 | >95 | >95 | >95 | >95 | >95 | >95 |

The data in Examples 67 to 77 demonstrate that capturing all the thermal power from combustion of a hydrogen sulfide stream that is produced from a feed gas stream containing hydrogen sulfide and carbon dioxide with the balance being hydrocarbons may generated all of the power required for separating the feed gas stream into a the hydrogen sulfide stream, a hydrocarbon gas stream, and a carbon dioxide stream and also produce sufficient power for processing the hydrocarbon gas stream to produce CNG and for processing the carbon dioxide stream to produce liquid carbon dioxide. Significant power for export may be generated as the volume of hydrogen sulfide in the feed gas stream exceeds about 10 volume %.

Comparative Examples 78 to 88

In a process model using process steps in accordance with the production of CNG using a conventional Claus process, power calculations for the production of 1142 metric tons of CNG per hour at a pressure of 24.1 MPa from selected feed gas streams containing from 0% to 63% by volume of hydrogen sulfide, from 0% to 32% by volume carbon dioxide, and from 100% to 5% by volume methane and having a pressure of 1.7 MPa were performed using energy consumption data obtained from known refinery process. In the process model, the feed gas stream was treated to separate water and liquid hydrocarbons from the feed gas stream. Next, hydrogen sulfide and carbon dioxide were removed from the feed gas stream using an amine extraction system to produce a methane-containing hydrocarbon gas stream. In the process model, the thermal power required to regenerate hydrogen sulfide from the hydrogen sulfide/carbon dioxide-loaded amine system was supplied as steam produced from Claus Process heat recovery unit(s) and operation of a supplemental boiler that was fueled by natural gas produced in the process. The boiler was assumed to have 100% thermal efficiency. In the process model, hydrogen sulfide produced from regeneration of the amine system was converted to elemental sulfur via the Claus Process. A heating value of 2973 Btu per pound (6915 kilojoule per kilogram) of elemental sulfur produced from the Claus Process was used in the calculations. A heating value for the regeneration of the hydrogen sulfide loaded amine extraction solution of 4030 Btu per pound (9374 kilojoule per kilogram) of hydrogen sulfide produced was used in the calculations. A heating value for the regeneration of carbon dioxide from the carbon dioxide loaded amine extraction solution of 1569 Btu per pound (3650 kilojoule per kilogram) of carbon dioxide was used in the calculations. A power requirement for carbon dioxide compression, liquefaction, and pumping of 0.11 MW per mT/h was used in the calculations. In the process model, if supplemental power was necessary methane was used as fuel. The consumption of methane was estimated using the lower heating value of 21433 Btu per pound (49820 kilojoule per kilogram) of methane.

In the process model, the methane-containing hydrocarbon gas stream produced by separation of hydrogen sulfide and carbon dioxide from the feed gas stream is processed to produce compressed natural gas (CNG). The power intensive step included in the process model for processing the hydrocarbon gas stream to form the CNG was compressing the hydrocarbon gas stream to a pressure of 24.1 MPa to form the CNG, where the hydrocarbon gas stream to be compressed has an initial pressure of 1.7 MPa. Other steps included in forming CNG such as separating heavier hydrocarbons from the hydrocarbon gas stream, removing metals from the hydrocarbon gas stream, dehydrating the hydrocarbon gas stream, and separating non-hydrocarbon gases from the hydrocarbon gas stream were excluded from the process model from an energy/power perspective since the power required to effect these steps is very small relative to the power required to effect the steps of separating/regenerating hydrogen sulfide and carbon dioxide using an amine system, liquefying the separated carbon dioxide, and compressing the hydrocarbon gas stream to form the CNG. In the process model, the thermal power required to compress the hydrocarbon gas stream to form the pipeline gas was provided from the Claus process heat recovery unit(s) and, if necessary, the supplemental boiler in which methane produced by the process was burned. TABLE 8 lists power data, CNG production data, elemental sulfur data, and carbon dioxide emission data for the production of CNG from the selected feed gas streams utilizing the Claus process. As shown in TABLE 8, the amount of carbon dioxide emission increases significantly as the amount of methane required for supplemental power is increased for feed gas streams that contain higher quantities of hydrogen sulfide and carbon dioxide, and lesser quantities of methane.

By comparing the data in Examples 67 to 77 to the data in Comparative Examples 78 to 88, it is shown that the use of hydrogen sulfide as fuel to power the separation of hydrogen sulfide and carbon dioxide from a feed gas stream to produce a hydrocarbon gas stream and the subsequent compression of the hydrocarbon gas stream to CNG, and liquefaction of the separated carbon dioxide yields most, and typically all, of the power required by those processes and may permit production of power for export. Conventional processes for producing CNG from streams containing significant amounts of hydrogen sulfide and carbon dioxide that utilize the Claus process to form elemental sulfur from hydrogen sulfide, however, require supplemental combustion of methane and associated emissions of carbon dioxide to meet the overall energy requirements of the process.

Examples 89 to 99

In a process model using process steps in accordance with a process of the present invention, power calculations for the production of 1142 metric tons of pipeline gas per hour (compressed to a pressure of 12.1 MPa (1750 psig)) from selected feed gas streams containing hydrocarbons and having from 5% to 95% by volume hydrogen sulfide and having a pressure of 1.7 MPa (250 psig) were performed using energy consumption data obtained from known refinery processes. In the process model, a selected feed gas stream was treated to separate water and liquid hydrocarbons from the feed gas stream. Next, hydrogen sulfide was removed from the feed gas stream using an amine extraction system to produce the hydrocarbon gas stream. The power required to regenerate the hydrogen sulfide from the hydrogen sulfide-loaded amine system was supplied as steam produced in a boiler. The boiler was assumed to have 100% thermal efficiency. In the process model, the thermal power for the boiler was produced by combusting the entire recovered hydrogen sulfide stream with an oxidant containing molecular oxygen, wherein the molar ratio of the molecular oxygen to the hydrogen sulfide was 1.5:1. The lower heating value of 6545 Btu per pound (15213 kilojoule per kilogram) of hydrogen sulfide was used in the calculations. A heating value for the regeneration of the hydrogen sulfide-loaded amine extraction solution of 4030 Btu per pound (9374 kilojoule per kilogram) of hydrogen sulfide produced was used in the calculations. In the process model, if supplemental power was necessary, methane was used as fuel. In the calculations, the consumption of methane was estimated using the lower heating value of 21433 Btu per pound (49820 kilojoule per kilogram) of methane.

In the process model, the hydrocarbon gas stream produced by separation of hydrogen sulfide from the feed gas stream is

TABLE 8

| Comparative Example No. | 78 | 79 | 80 | 81 | 82 | 83 | 84 | 85 | 86 | 87 | 88 |
|---|---|---|---|---|---|---|---|---|---|---|---|
| Volume %, $H_2S$ | 0 | 6.6 | 13.2 | 19.8 | 26.4 | 33 | 39.6 | 46.2 | 52.8 | 59.4 | 62.7 |
| Volume %, $CO_2$ | 0 | 3.4 | 6.8 | 10.2 | 13.6 | 17 | 20.4 | 23.8 | 27.2 | 30.6 | 32.3 |
| Volume %, $CH_4$ | 100 | 90 | 80 | 70 | 60 | 50 | 40 | 30 | 20 | 10 | 5 |
| CNG Produced, mT/h | 1142 | 1142 | 1142 | 1142 | 1142 | 1142 | 1142 | 1142 | 1142 | 1142 | 1142 |
| Elemental Sulfur Produced, mT/h | 0 | 167 | 377 | 646 | 1005 | 1507 | 2260 | 3516 | 6027 | 13562 | 28630 |
| Power Generated by Claus Plant, MWt | 0 | 321 | 723 | 1240 | 1929 | 2893 | 4340 | 6750 | 11572 | 26037 | 54968 |
| Power Required To Separate $H_2S$ and $CO_2$, MWt | 0 | 583 | 1313 | 2250 | 3500 | 5250 | 7876 | 12251 | 21002 | 47254 | 99759 |
| Power Required To Make CNG, MWt | 316 | 316 | 316 | 316 | 316 | 316 | 316 | 316 | 316 | 316 | 316 |
| Supplemental Power Required, MWt | 316 | 578 | 905 | 1326 | 1888 | 2674 | 3852 | 5817 | 9746 | 21533 | 45107 |
| Methane Required for Supplemental Power, mT/h | 23 | 42 | 65 | 96 | 136 | 193 | 278 | 420 | 704 | 1556 | 3259 |
| Total Carbon Dioxide Emitted, mT/h | 63 | 233 | 447 | 721 | 1087 | 1599 | 2366 | 3646 | 6206 | 13884 | 29242 | processed to produce pipeline gas. The power intensive step included in the process model for processing the hydrocarbon gas stream to form pipeline gas was compressing the hydrocarbon gas stream to a pressure of 12.1 MPa to form the pipeline gas. In the process model, the thermal power required to compress the hydrocarbon gas stream was provided from the boiler in which the hydrogen sulfide was combusted.

TABLE 9 lists power data, pipeline gas production data, sulfur dioxide production data, and carbon dioxide emission data from the selected feed gas streams containing hydrocarbons and from 5% to 95% by volume hydrogen sulfide. Using the values in TABLE 9, the maximum amount of thermal power available upon separation and combustion of hydrogen sulfide from the selected feed gas streams (basis production of 1142 metric tons of pipeline gas at 12.1 MPa per hour) was calculated to be 207 MWt at 5% $H_2S$, 437 MWt at 10% $H_2S$, 984 MWt at 20% $H_2S$, 1687 MWt at 30% $H_2S$, 2624 MWt at 40% $H_2S$, 3936 MWt at 50% $H_2S$, 5905 MWt at 60% $H_2S$, 9185 MWt at 70% $H_2S$, 15746 MWt at 80% $H_2S$, 35428 MWt at 90% $H_2S$ and 74793 MWt at 95% $H_2S$ [available thermal power=thermal power generated from combustion of $H_2S$ minus power consumed to separate hydrogen sulfide from the feed gas stream]. The amount of excess power generated by combusting hydrogen sulfide separated from the selected feed gas streams and providing a portion of the thermal power produced thereby sufficient to separate the hydrogen sulfide from the feed gas stream to produce a hydrocarbon gas stream and to process the hydrocarbon gas stream to produce pipeline gas (basis production of 1142 metric tons of pipeline gas at 12.1 MPa per hour) was calculated to be 61 MWt at 5% $H_2S$, 291 MWt at 10% $H_2S$, 838 MWt at 20% $H_2S$, 1541 MWt at 30% $H_2S$, 2478 MWt at 40% $H_2S$, 3791 MWt at 50% $H_2S$, 5759 MWt at 60% $H_2S$, 9039 MWt at 70% $H_2S$, 15600 MWt at 80% $H_2S$, 35282 MWt at 90% $H_2S$, and 74647 MWt at 95% $H_2S$ [excess thermal power=(thermal power generated by combustion of hydrogen sulfide) minus (power consumed to separate hydrogen sulfide from the feed gas stream plus power consumed to compress the hydrocarbon gas stream to produce pipeline gas)].

The data in Examples 89 to 99 demonstrate generation of thermal power from combustion of a hydrogen sulfide stream with an oxidant at a molar ratio of molecular oxygen to hydrogen sulfide of 1.5:1, where the hydrogen sulfide stream is separated from a feed gas stream containing hydrocarbons and at least 5 vol. % hydrogen sulfide, where a hydrocarbon gas stream is also separated from the feed gas stream and the hydrocarbon gas stream is processed to produce pipeline gas, and where the thermal power is utilized in the steps of separating the feed gas stream into the hydrogen sulfide stream and the hydrocarbon gas stream and processing the hydrocarbon gas stream to produce pipeline gas.

The data in Examples 89 to 99 also demonstrate generation of thermal power from combustion of more than one third of a hydrogen sulfide stream with an oxidant at a molar ratio of molecular oxygen to hydrogen sulfide of 1.5 to 1, where the hydrogen sulfide stream is separated from a feed gas stream containing hydrocarbons and at least 5 vol. % hydrogen sulfide, where a hydrocarbon gas stream is also separated from the feed gas stream and the hydrocarbon gas stream is processed to produce pipeline gas.

Furthermore, the data in Examples 89 to 99 demonstrates that the process of the present invention utilizing a feed gas stream containing hydrocarbons and at least 5 vol. % hydrogen sulfide generates 540 $MW_t$ of thermal power, of which over 60 $MW_t$ of thermal power is generated in excess of the power required to separate the feed gas stream into a hydrocarbon gas stream and a hydrogen sulfide stream and to process the hydrocarbon gas stream to produce pipeline gas. Upon conversion of the excess thermal power to electrical power, at least 25 megawatts of electric power is available for export as electricity at a 40% efficiency while at most 0.1 grams of carbon dioxide per gram of hydrocarbons in the feed gas stream are produced during combustion of the hydrogen sulfide.

Comparative Examples 100 to 110

In a process model using process steps in accordance with the production of pipeline gas using a conventional Claus process, power calculations for the production of 1142 metric tons per hour of pipeline gas at a pressure of 12.1 MPa from selected feed gas streams containing methane and from 5 vol. % to 95 vol. % hydrogen sulfide and having a pressure of 1.7 MPa were performed using energy consumption data obtained from a known refinery process. In the process

TABLE 9

| Illustrative Example No. | 89 | 90 | 91 | 92 | 93 | 94 | 95 | 96 | 97 | 98 | 99 |
|---|---|---|---|---|---|---|---|---|---|---|---|
| Volume %, $H_2S$ | 5 | 10 | 20 | 30 | 40 | 50 | 60 | 70 | 80 | 90 | 95 |
| Volume %, $CH_4$ | 95 | 90 | 80 | 70 | 60 | 50 | 40 | 30 | 20 | 10 | 5 |
| Pipeline Gas Produced, mT/h | 1142 | 1142 | 1142 | 1142 | 1142 | 1142 | 1142 | 1142 | 1142 | 1142 | 1142 |
| Sulfur Dioxide Produced, mT/h | 240 | 507 | 1142 | 1957 | 3044 | 4566 | 6849 | 10654 | 18265 | 41096 | 86758 |
| Power Generated By $H_2S$ Burning, MWt | 540 | 1139 | 2563 | 4394 | 6835 | 10253 | 15380 | 23924 | 41012 | 92278 | 194809 |
| Power Required To Separate $H_2S$, MWt | 332 | 702 | 1579 | 2707 | 4211 | 6317 | 9475 | 14739 | 25267 | 56850 | 120016 |
| Excess Power After Purifying Natural Gas, MWt | 207 | 437 | 984 | 1687 | 2624 | 3936 | 5905 | 9185 | 15746 | 35428 | 74793 |
| Power Required To Make Pipeline Gas, MWt | 146 | 146 | 146 | 146 | 146 | 146 | 146 | 146 | 146 | 146 | 146 |
| Excess Power Produced After Making Pipeline Gas, MWt | 61 | 291 | 838 | 1541 | 2478 | 3791 | 5759 | 9039 | 15600 | 35282 | 74647 |
| Power Export at 40% Efficiency After Making Pipeline Gas, MWe | 25 | 117 | 335 | 616 | 991 | 1516 | 2304 | 3616 | 6240 | 14113 | 29859 |
| Power Export at 60% Efficiency After Making Pipeline Gas, MWe | 37 | 175 | 503 | 925 | 1487 | 2274 | 3455 | 5424 | 9360 | 21169 | 44788 |
| Power Exported After Making Pipeline Gas, kWh/kg $H_2S$ | 0.5 | 1.1 | 1.4 | 1.5 | 1.5 | 1.6 | 1.6 | 1.6 | 1.6 | 1.6 | 1.6 |
| Supplemental Power Required, MWt | 0 | 0 | 0 | 0 | 0 | 0 | 0 | 0 | 0 | 0 | 0 |
| Methane Required for Supplemental Power, mT/h | 0 | 0 | 0 | 0 | 0 | 0 | 0 | 0 | 0 | 0 | 0 |
| Carbon Dioxide Emitted, mT/h | 0 | 0 | 0 | 0 | 0 | 0 | 0 | 0 | 0 | 0 | 0 | model, the feed gas stream was treated to separate water and liquid hydrocarbons from the feed gas stream. Next, hydrogen sulfide was removed from the feed gas stream using an amine extraction system to produce a hydrocarbon gas stream. In the process model, the thermal power required to regenerate hydrogen sulfide from the hydrogen sulfide-loaded amine system was supplied as steam produced from Claus Process heat recovery unit(s) and operation of a supplemental boiler that was fueled by natural gas produced in the process. The boiler was assumed to have 100% thermal efficiency. In the process model, hydrogen sulfide produced from regeneration of the amine system was converted to elemental sulfur via the Claus Process. A heating value of 2973 Btu per pound (6915 kilojoule per kilogram) of elemental sulfur produced from the Claus Process was used in the calculations. A heating value for the regeneration of the hydrogen sulfide loaded amine extraction solution of 4030 Btu per pound (9374 kilojoule per kilogram) of hydrogen sulfide produced was used in the calculations. In the process model, methane was used as fuel for generating supplemental power. The consumption of methane was estimated using the lower heating value of 21433 Btu per pound (49820 kilojoule per kilogram) of methane.

In the process model, the hydrocarbon gas stream produced by separation of hydrogen sulfide from the feed gas stream is processed to produce pipeline gas. The power intensive step included in the process model for processing the hydrocarbon gas stream to form pipeline gas was compressing the hydrocarbon gas stream to a pressure of 12.1 MPa to form the pipeline gas. In the process model, the thermal power required to compress the hydrocarbon gas stream to form the pipeline gas was provided from the Claus process heat recovery unit(s) and, if necessary, the supplemental boiler in which methane produced by the process was burned.

TABLE 10 lists power data, pipeline gas production data, elemental sulfur production data, and carbon dioxide emission data for the production of pipeline gas from the selected feed gas streams utilizing the conventional Claus process. As shown in TABLE 10 the amount of methane fuel required for supplemental power for hydrogen sulfide separation and to produce pipeline gas increases significantly as the amount of hydrogen sulfide in the feed stream increases.

lize the Claus process to produce elemental sulfur from hydrogen sulfide, however, typically require supplemental combustion of methane and associated emission of carbon dioxide to meet the overall power requirements for the production of pipeline gas.

Examples 111 to 121

In a process model using process steps in accordance with a process of the present invention, power calculations for the production of 1142 metric tons per hour of pipeline gas at a pressure of 12.1 MPa from selected feed gas streams containing from 0% to 63% by volume of hydrogen sulfide, from 0% to 32% by volume carbon dioxide, and from 100% to 5% by volume methane and having a pressure of 1.7 MPa were performed using energy consumption data obtained from known refinery processes. In the process model, the selected feed gas stream was treated to separate water and liquid hydrocarbons from the feed gas stream. Next, hydrogen sulfide and carbon dioxide were removed from the feed gas stream using an amine extraction system to produce a hydrocarbon gas stream. In the process model, the thermal power required to regenerate hydrogen sulfide and carbon dioxide from the hydrogen sulfide/carbon dioxide-loaded amine system was supplied as steam produced in a boiler. The boiler was assumed to have 100% thermal efficiency. In the process model, the thermal energy for the boiler was produced by combusting the entire recovered hydrogen sulfide stream with an oxidant containing molecular oxygen, wherein the molar ratio of molecular oxygen to hydrogen sulfide was 1.5:1. The lower heating value of 6545 Btu per pound (15213 kilojoule per kilogram) of hydrogen sulfide was used in the calculations. A heating value for the regeneration of the hydrogen sulfide loaded amine extraction solution of 4030 Btu per pound (9374 kilojoule per kilogram) of hydrogen sulfide produced was used in the calculations. A heating value for the regeneration of the carbon dioxide loaded amine extraction solution of 1569 Btu per pound (3650 kilojoule per kilogram) of carbon dioxide, as described by Lars Erik Øi, in, "Aspen HYSYS Simulation of $CO_2$ Removal by Amine Absorption from a Gas Based Power Plant" SIMS2007 Conference,

TABLE 10

| Comparative Example No. | 100 | 101 | 102 | 103 | 104 | 105 | 106 | 107 | 108 | 109 | 110 |
|---|---|---|---|---|---|---|---|---|---|---|---|
| Volume %, $H_2S$ | 0 | 10 | 20 | 30 | 40 | 50 | 60 | 70 | 80 | 90 | 95 |
| Volume %, $CH_4$ | 100 | 90 | 80 | 70 | 60 | 50 | 40 | 30 | 20 | 10 | 5 |
| Pipeline Gas Produced, mT/h | 1142 | 1142 | 1142 | 1142 | 1142 | 1142 | 1142 | 1142 | 1142 | 1142 | 1142 |
| Elemental Sulfur Produced, mT/h | 0 | 254 | 571 | 978 | 1522 | 2283 | 3425 | 5327 | 9132 | 20548 | 43379 |
| Power Generated By Claus Plant, MWt | 0 | 487 | 1096 | 1879 | 2922 | 4383 | 6575 | 10228 | 17534 | 39451 | 83285 |
| Power Required To Separate $H_2S$, MWt | 0 | 702 | 1579 | 2707 | 4211 | 6317 | 9475 | 14739 | 25267 | 56850 | 120016 |
| Power Required To Make Pipeline Gas, MWt | 146 | 146 | 146 | 146 | 146 | 146 | 146 | 146 | 146 | 146 | 146 |
| Supplemental Power Required, MWt | 146 | 361 | 629 | 974 | 1435 | 2079 | 3046 | 4657 | 7879 | 17545 | 36877 |
| Methane for Supplemental Power, mT/h | 11 | 26 | 45 | 70 | 104 | 150 | 220 | 336 | 569 | 1268 | 2664 |
| Carbon Dioxide Emitted, mT/h | 29 | 72 | 125 | 194 | 285 | 413 | 605 | 925 | 1565 | 3486 | 7327 |

By comparing the data in Examples 89 to 99 to the data in Comparative Examples 100 to 110, it is shown that the use of hydrogen sulfide as fuel to power the separation of the feed gas stream into a hydrogen sulfide stream and a hydrocarbon gas stream and to process the hydrocarbon gas stream to produce pipeline gas typically yields more thermal power than is required by those process steps and permits production of electrical power for export as electricity. Conventional processes for producing pipeline gas from feed gas streams containing significant amounts of hydrogen sulfide that uti- Gøteborg, Sweden, Oct. 30 and 31, 2007, was used in the calculations. The power requirement for carbon dioxide compression, liquefaction, and pumping was estimated to be 0.11 MW per mT/h, as described by Baldwin et al. in "Capturing $CO_2$: Gas Compression vs. Liquefaction," Power, June 2009, electronic publication. In the process model, if supplemental power was necessary methane was used as fuel. The consumption of methane was estimated using the lower heating value of 21433 Btu per pound (49820 kilojoule per kilogram) of methane.

In the process model, the hydrocarbon gas stream produced by separation of hydrogen sulfide and carbon dioxide from the feed gas stream is processed to produce pipeline gas. The power intensive step included in the process model for processing the hydrocarbon gas stream to form pipeline gas was compressing the hydrocarbon gas stream to a pressure of 12.1 MPa to form the pipeline gas. In the process model, the thermal power required to compress the hydrocarbon gas stream was provided from the boiler in which the hydrogen sulfide was combusted.

TABLE 11 lists power data, pipeline gas production data, sulfur dioxide production data, and carbon dioxide emission data for the production of pipeline gas from the selected feed gas streams using combustion of hydrogen sulfide as a source of power. Using the values in TABLE 11, the amount of excess thermal power generated by combusting hydrogen sulfide separated from the selected feed gas streams and providing a portion of the thermal power produced thereby sufficient to separate the hydrogen sulfide and carbon dioxide from the feed gas stream to produce a hydrocarbon gas stream and process the hydrocarbon gas stream to produce a pipeline gas (basis production of 1142 metric tons of pipeline gas per hour at 12.1 MPa from a feed gas stream having a pressure of 1.7 MPa) was calculated to be 23 MWt at 90% methane, 6.6% $H_2S$, and 3.4% $CO_2$; 233 MWt at 80%, 13.2%, and 6.8% $CH_4$, $H_2S$, and $CO_2$ respectively; 504 MWt at 70%, 19.8%, and 10.2% $CH_4$, $H_2S$, and $CO_2$ respectively; 865 MWt at 60%, 26.4%, and 13.6% $CH_4$, $H_2S$, and $CO_2$ respectively; 1371 MWt at 50%, 33%, and 17% $CH_4$, $H_2S$, and $CO_2$ respectively; 2129 MWt at 40%, 39.6%, and 20.4% $CH_4$, $H_2S$, and $CO_2$ respectively; 3393 MWt at 30%, 46.2%, and 20.4% $CH_4$, $H_2S$, and $CO_2$ respectively; 5920 MWt at 20%, 52.8%, and 27.2% $CH_4$, $H_2S$, and $CO_2$ respectively; 13503 MWt at 10%, 59.4%, and 30.6% $CH_4$, $H_2S$, and $CO_2$ respectively; and 28669 MWt at 5%, 62.7%, and 32.3% $CH_4$, $H_2S$, and $CO_2$ respectively respectively [excess thermal power=(thermal power generated from combustion of separated hydrogen sulfide) minus (thermal power consumed to separate hydrogen sulfide, carbon dioxide, and the hydrocarbon gas stream from the feed gas stream plus thermal power consumed to compress the separated hydrocarbon gas stream to form pipeline gas)]. The amount of excess thermal power generated by combustion of hydrogen sulfide from the selected feed gas streams and providing a portion of the thermal power produced thereby sufficient to separate the hydrogen sulfide, carbon dioxide, and hydrocarbon gas stream from the feed gas stream, and to liquefy the separated carbon dioxide, and to process the hydrocarbon gas stream to produce pipeline gas (basis production of 1142 metric tons of pipeline gas per hour at 12.1 MPa from a feed gas steam at a pressure of 1.7 MPa) was calculated to be 10 MWt at 90% methane, 6.6% $H_2S$, and 3.4% $CO_2$; 204 MWt at 80%, 13.2%, and 6.8% $CH_4$, $H_2S$, and $CO_2$ respectively; 454 MWt at at 70%, 19.8%, and 10.2% $CH_4$, $H_2S$, and $CO_2$ respectively; 787 MWt at 60%, 26.4%, and 13.6% $CH_4$, $H_2S$, and $CO_2$ respectively; 1253 MWt at 50%, 33%, and 17% $CH_4$, $H_2S$, and $CO_2$ respectively; 1953 MWt at 40%, 39.6%, and 20.4% $CH_4$, $H_2S$, and $CO_2$ respectively; 3119 MWt at 30%, 46.2%, and 20.4% $CH_4$, $H_2S$, and $CO_2$ respectively; 5451 MWt at 20%, 52.8%, and 27.2% $CH_4$, $H_2S$, and $CO_2$ respectively; 12447 MWt at 10%, 59.4%, and 30.6% $CH_4$, $H_2S$, and $CO_2$ respectively; and 26438 MWt at 5%, 62.7%, and 32.3% $CH_4$, $H_2S$, and $CO_2$ respectively [excess thermal power=(thermal power generated from combustion of separated hydrogen sulfide) minus (thermal power consumed to separate hydrogen sulfide, carbon dioxide, and hydrocarbon gas stream from the feed gas stream plus thermal power consumed to compress the separated hydrocarbon gas stream to form pipeline gas plus thermal power consumed to liquefy $CO_2$)].

TABLE 11

| Illustrative Example No. | 111 | 112 | 113 | 114 | 115 | 116 | 117 | 118 | 119 | 120 | 121 |
|---|---|---|---|---|---|---|---|---|---|---|---|
| Volume %, $H_2S$ | 0 | 6.6 | 13.2 | 19.8 | 26.4 | 33 | 39.6 | 46.2 | 52.8 | 59.4 | 62.7 |
| Volume %, $CO_2$ | 0 | 3.4 | 6.8 | 10.2 | 13.6 | 17 | 20.4 | 23.8 | 27.2 | 30.6 | 32.3 |
| Volume %, $CH_4$ | 100 | 90 | 80 | 70 | 60 | 50 | 40 | 30 | 20 | 10 | 5 |
| Pipeline Gas Produced, mT/h | 1142 | 1142 | 1142 | 1142 | 1142 | 1142 | 1142 | 1142 | 1142 | 1142 | 1142 |
| Sulfur Dioxide Produced, mT/h | 0 | 335 | 753 | 1292 | 2009 | 3014 | 4521 | 7032 | 12055 | 27123 | 57260 |
| Carbon Dioxide Produced, mT/h | 0 | 119 | 267 | 457 | 712 | 1067 | 1601 | 2490 | 4269 | 9606 | 20280 |
| Power Generated by $H_2S$ Burning, MWt | 0 | 752 | 1692 | 2900 | 4511 | 6767 | 10151 | 15790 | 27068 | 60903 | 128574 |
| Power Required To Separate $H_2S$ and $CO_2$, MWt | 0 | 583 | 1313 | 2250 | 3500 | 5250 | 7876 | 12251 | 21002 | 47254 | 99759 |
| Excess Power After Purifying Natural Gas, MWt | 0 | 169 | 379 | 650 | 1011 | 1517 | 2275 | 3539 | 6066 | 13649 | 28815 |
| Power Required To Make Pipeline Gas, MWt | 146 | 146 | 146 | 146 | 146 | 146 | 146 | 146 | 146 | 146 | 146 |
| Excess Power After Making Pipeline Gas, MWt | 0 | 23 | 233 | 504 | 865 | 1371 | 2129 | 3393 | 5920 | 13503 | 28669 |
| Power Required To Liquefy $CO_2$, MWt | 0 | 13 | 29 | 50 | 78 | 117 | 176 | 274 | 470 | 1057 | 2231 |
| Excess Power After Making Pipeline Gas and $CO_2$(l), MWt | 0 | 10 | 204 | 454 | 787 | 1253 | 1953 | 3119 | 5451 | 12447 | 26438 |
| Supplemental Power Required, MWt | 146 | 0 | 0 | 0 | 0 | 0 | 0 | 0 | 0 | 0 | 0 |
| Methane Required For Supplemental Power, mT/h | 11 | 0 | 0 | 0 | 0 | 0 | 0 | 0 | 0 | 0 | 0 |
| Power Export at 40% Efficiency After Making Pipeline Gas & $CO_2$(l), MWe | 0 | 4 | 82 | 182 | 315 | 501 | 781 | 1248 | 2180 | 4979 | 10575 |
| Power Export at 60% Efficiency, After Making Pipeline Gas & $CO_2$(l), MWe | 0 | 6 | 122 | 272 | 472 | 752 | 1172 | 1871 | 3270 | 7468 | 15863 |
| Power Export After Making Pipeline Gas & $CO_2$(l), kWh/Kg $H_2S$ | 0 | 0.1 | 0.5 | 0.7 | 0.7 | 0.8 | 0.8 | 0.8 | 0.9 | 0.9 | 0.9 |
| Carbon Dioxide Emitted, mT/h | 29 | 0 | 0 | 0 | 0 | 0 | 0 | 0 | 0 | 0 | 0 |
| Carbon Dioxide Captured, % | | >95 | >95 | >95 | >95 | >95 | >95 | >95 | >95 | >95 | >95 |

The data in Examples 111 to 121 demonstrate that captured thermal power from combustion of a hydrogen sulfide stream that is produced from a feed gas stream containing hydrogen sulfide and carbon dioxide with the balance being hydrocarbons may provide most or all of the power required for separating the feed gas stream into a the hydrogen sulfide stream, a hydrocarbon gas stream, and a carbon dioxide stream and also provide sufficient power for processing the hydrocarbon gas stream to produce pipeline gas and for processing the separated carbon dioxide to produce liquid carbon dioxide. Significant power for export as thermal or mechanical or electrical power may be generated as the volume of hydrogen sulfide in the feed gas stream exceeds about 10 volume %.

Comparative Examples 122 to 132

In a process model using process steps in accordance with the production of pipeline gas using a conventional Claus process, power calculations for the production of 1142 metric tons per hour of pipeline gas at a pressure of 12.1 MPa from selected feed gas streams containing from 0% to 63% by volume of hydrogen sulfide, from 0% to 32% by volume carbon dioxide, and from 100% to 5% by volume methane and having a pressure of 1.7 MPa were performed using energy consumption data obtained from known refinery process. In the process model, the feed gas stream was treated to separate water and liquid hydrocarbons from the feed gas stream. Next, hydrogen sulfide and carbon dioxide were removed from the feed gas stream using an amine extraction system to produce a hydrocarbon gas stream. In the process model, the thermal power required to regenerate hydrogen sulfide from the hydrogen sulfide/carbon dioxide-loaded amine system was supplied as steam produced from Claus Process heat recovery unit(s) and operation of a supplemental boiler that was fueled by natural gas produced in the process. The boiler was assumed to have 100% thermal efficiency. In the process model, hydrogen sulfide produced from regeneration of the amine system was converted to elemental sulfur via the Claus Process. A heating value of 2973 Btu per pound (6915 kilojoule per kilogram) of elemental sulfur produced from the Claus Process was used in the calculations. A heating value for the regeneration of the hydrogen sulfide loaded amine extraction solution of 4030 Btu per pound (9374 kilojoule per kilogram) of hydrogen sulfide produced was used in the calculations. A heating value for the regeneration of the carbon dioxide loaded amine extraction solution of 1569 Btu per pound (3650 kilojoule per kilogram) of carbon dioxide was used in the calculations. A power requirement for carbon dioxide compression, liquefaction, and pumping of 0.11 MW per mT/h was used in the calculations. In the process model, if supplemental power was necessary methane was used as fuel. The consumption of methane was estimated using the lower heating value of 21433 Btu per pound (49820 kilojoule per kilogram) of methane.

In the process model, the hydrocarbon gas stream produced by separation of hydrogen sulfide and carbon dioxide from the feed gas stream is processed to produce pipeline gas. The power intensive step included in the process model for processing the hydrocarbon gas stream to form pipeline gas was compressing the hydrocarbon gas stream to a pressure of 12.1 MPa to form the pipeline gas. In the process model, the thermal power required to compress the hydrocarbon gas stream to form the pipeline gas was provided from the Claus process heat recovery unit(s) and, if necessary, the supplemental boiler in which methane produced by the process was burned.

TABLE 12 lists power data, pipeline gas production data, elemental sulfur data, and carbon dioxide emission data for the production of pipeline gas from the selected feed gas streams utilizing the conventional Claus process. As shown in TABLE 12, the amount of carbon dioxide emission increases significantly as the amount of methane required for supplemental power is increased for streams that contain higher quantities of hydrogen sulfide and carbon dioxide, and lesser quantities of methane.

TABLE 12

| Comparative Example No. | 122 | 123 | 124 | 125 | 126 | 127 | 128 | 129 | 130 | 131 | 132 |
|---|---|---|---|---|---|---|---|---|---|---|---|
| Volume %, $H_2S$ | 0 | 6.6 | 13.2 | 19.8 | 26.4 | 33 | 39.6 | 46.2 | 52.8 | 59.4 | 62.7 |
| Volume %, $CO_2$ | 0 | 3.4 | 6.8 | 10.2 | 13.6 | 17 | 20.4 | 23.8 | 27.2 | 30.6 | 32.3 |
| Volume %, $CH_4$ | 100 | 90 | 80 | 70 | 60 | 50 | 40 | 30 | 20 | 10 | 5 |
| Pipeline Gas Produced, mT/h | 1142 | 1142 | 1142 | 1142 | 1142 | 1142 | 1142 | 1142 | 1142 | 1142 | 1142 |
| Elemental Sulfur Produced, mT/h | 0 | 167 | 377 | 646 | 1005 | 1507 | 2260 | 3516 | 6027 | 13562 | 28630 |
| Power Generated by Claus Plant, MWt | 0 | 321 | 723 | 1240 | 1929 | 2893 | 4340 | 6750 | 11572 | 26037 | 54968 |
| Power Required To Separate $H_2S$ and $CO_2$, MWt | 0 | 583 | 1313 | 2250 | 3500 | 5250 | 7876 | 12251 | 21002 | 47254 | 99759 |
| Power Required To Make Pipeline Gas, MWt | 146 | 146 | 146 | 146 | 146 | 146 | 146 | 146 | 146 | 146 | 146 |
| Supplemental Power Required, MWt | 146 | 408 | 735 | 1156 | 1718 | 2503 | 3682 | 5647 | 9576 | 21363 | 44937 |
| Methane Required for Supplemental Power, mT/h | 11 | 29 | 53 | 84 | 124 | 181 | 266 | 408 | 692 | 1543 | 3247 |
| Total Carbon Dioxide Emitted, mT/h | 29 | 200 | 413 | 687 | 1053 | 1565 | 2333 | 3612 | 6172 | 13851 | 29208 |

By comparing the data in Examples 111 to 121 to the data in Comparative Examples 122 to 132, it is shown that the use of hydrogen sulfide as fuel to power the separation of hydrogen sulfide and carbon dioxide from a feed gas stream, to produce pipeline gas and to liquefy separated carbon dioxide yields most, and typically all, of the power required by those processes and may permit production of electrical power for export. Conventional processes for producing pipeline gas from streams containing significant amounts of hydrogen sulfide and carbon dioxide that utilize the Claus process to form elemental sulfur from hydrogen sulfide, however, typically require supplemental combustion of methane and associated emissions of carbon dioxide to meet the overall energy requirements of the process.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. While compositions and methods are described in terms of "comprising," "containing," or "including" various components or steps, the compositions and methods can also "consist essentially of" or "consist of" the various components and steps. Whenever a numerical range with a lower limit and an upper limit is disclosed, any number and any included range falling within the range is specifically disclosed. In particular, every range of values (of the form, "from a to b," or, equivalently, "from a-b") disclosed herein is to be understood to set forth every number and range encompassed within the broader range of values. Whenever a numerical range having a specific lower limit only, a specific upper limit only, or a specific upper limit and a specific lower limit is disclosed, the range also includes any numerical value "about" the specified lower limit and/or the specified upper limit. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces.

What is claimed is:

1. A method, comprising:
   providing a feed gas stream comprising hydrogen sulfide and hydrocarbons, wherein the feed gas stream comprises at least 5% by volume hydrogen sulfide;
   separating at least a portion of the feed gas stream into a hydrogen sulfide stream and a hydrocarbon gas stream, the hydrogen sulfide stream containing more hydrogen sulfide, by volume percent, than the feed gas stream, and the hydrocarbon gas stream containing less hydrogen sulfide, by volume percent, than the feed gas stream;
   processing the hydrocarbon gas stream to produce natural gas; and
   combusting at least 34 mol % of the hydrogen sulfide in the hydrogen sulfide stream with an oxidant containing molecular oxygen to generate thermal power, where the molar ratio of molecular oxygen to hydrogen sulfide in the hydrogen sulfide stream and oxidant that are combusted is at least 1.4 to 1;
   utilizing the thermal power in one or more of the steps of separating the feed gas stream into the hydrogen sulfide stream and the hydrocarbon gas stream.

2. The method of claim 1, wherein processing the hydrocarbon gas stream to produce natural gas comprises performing one or more of the steps of:
   a) dehydrating the hydrocarbon gas stream;
   b) removing metals from the hydrocarbon gas stream;
   c) separating non-hydrocarbon gases from the hydrocarbon gas stream;
   d) separating natural gas liquids from the hydrocarbon gas stream and
   e) compressing the hydrocarbon gas stream to a pressure of from 1.7 MPa to 12.1 MPa.

3. The method of claim 1 wherein the thermal power generated by combusting the hydrogen sulfide stream is utilized to provide all of the power required for separating the feed gas stream into the hydrogen sulfide stream and the hydrocarbon gas stream, for processing the hydrocarbon gas stream to produce the natural gas.

4. The method of claim 1 wherein combustion of the hydrogen sulfide stream generates at most 0.1 grams of carbon dioxide per gram of hydrocarbons in the feed gas stream.

5. The method of claim 1 further comprising transporting to one or more facilities at least 90% of the natural gas.

6. The method of claim 1 wherein the thermal power generated by combustion of the hydrogen sulfide portion of the hydrogen sulfide stream is at least 100 MW.

7. The method of claim 1 wherein at least a portion of the thermal power generated by combustion of the hydrogen sulfide stream is converted to electrical power.

8. The method of claim 1 wherein at least a portion of the thermal power generated by combustion of the hydrogen sulfide stream is converted to mechanical power.

9. A method, comprising:
   providing a feed gas stream comprising hydrogen sulfide and hydrocarbons, wherein the feed gas stream comprises at least 5% by volume hydrogen sulfide;
   separating at least a portion of the feed gas stream into a hydrogen sulfide stream and a hydrocarbon gas stream, the hydrogen sulfide stream containing more hydrogen sulfide, by volume percent, than the feed gas stream, and the hydrocarbon gas stream containing less hydrogen sulfide, by volume percent, than the feed gas stream;
   processing the hydrocarbon gas stream to produce compressed natural gas; and
   combusting at least 34 mol % of hydrogen sulfide in the hydrogen sulfide stream with an oxidant containing molecular oxygen to generate thermal power, where the molar ratio of molecular oxygen to hydrogen sulfide in the hydrogen sulfide stream and oxidant that are combusted is at least 1.4 to 1; and
   utilizing the thermal power in one or more of the steps of separating the feed gas stream into the hydrogen sulfide stream and the hydrocarbon gas stream.

10. The method of claim 9, wherein processing the hydrocarbon gas stream to produce compressed natural gas comprises performing one or more of the steps of:
    a) dehydrating the hydrocarbon gas stream;
    b) removing metals from the hydrocarbon gas stream;
    c) separating non-hydrocarbon gases from the hydrocarbon gas stream;
    d) separating natural gas liquids from the hydrocarbon gas stream and
    e) compressing the hydrocarbon gas stream to a pressure of from 13.8 MPa to 27.6 MPa.

11. The method of claim 9 wherein the thermal power generated by combusting the hydrogen sulfide stream is utilized to provide all of the power required for separating the feed gas stream into the hydrogen sulfide stream and the hydrocarbon gas stream, for processing the hydrocarbon gas stream to produce the compressed natural gas.

12. The method of claim 9 wherein at least a portion of the thermal power generated by combustion of the hydrogen sulfide stream is converted to electrical power.

13. The method of claim 9 wherein at least a portion of the thermal power generated by combustion of the hydrogen sulfide stream is converted to mechanical power.

14. The method of claim 9, wherein combustion of the hydrogen sulfide stream generates at most 0.1 grams of carbon dioxide per gram of hydrocarbons in the feed gas stream.

15. A method, comprising:
    providing a feed gas stream comprising hydrogen sulfide and hydrocarbons, wherein the feed gas stream comprises at least 5% by volume hydrogen sulfide;
    separating at least a portion of the feed gas stream into a hydrogen sulfide stream and a hydrocarbon gas stream, the hydrogen sulfide stream containing more hydrogen sulfide, by volume percent, than the feed gas stream, and the hydrocarbon gas stream containing less hydrogen sulfide, by volume percent, than the feed gas stream;
    processing the hydrocarbon gas stream to produce liquefied natural gas; and
    combusting at least 34 mol % of hydrogen sulfide in the hydrogen sulfide stream with an oxidant containing molecular oxygen to generate thermal power, where the molar ratio of molecular oxygen to hydrogen sulfide in the hydrogen sulfide stream and oxidant that are combusted is at least 1.4 to 1;
    utilizing the thermal power in one or more of the steps of separating the feed gas stream into the hydrogen sulfide stream and the hydrocarbon gas stream.

16. The method of claim 15, wherein processing the hydrocarbon gas stream to produce liquefied natural gas comprises performing one or more of the steps of:
    a) dehydrating the hydrocarbon gas stream;
    b) removing metals from the hydrocarbon gas stream;

c) separating non-hydrocarbon gases from the hydrocarbon gas stream;
d) separating natural gas liquids from the hydrocarbon gas stream and
e) compressing the hydrocarbon gas stream to a pressure of at least 5.5 MPa;
f) liquefying the compressed gas stream.

17. The method of claim 15 wherein the thermal power generated by combusting the hydrogen sulfide stream is utilized to provide all of the power required for separating the feed gas stream into the hydrogen sulfide stream and the hydrocarbon gas stream, for processing the hydrocarbon gas stream to produce the liquefied natural gas.

18. The method of claim 15 wherein at least a portion of the thermal power generated by combustion of the hydrogen sulfide stream is converted to electrical power.

19. The method of claim 15 wherein at least a portion of the thermal power generated by combustion of the hydrogen sulfide stream is converted to mechanical power.

20. The method of claim 15, wherein combustion of the hydrogen sulfide stream generates at most 0.1 grams of carbon dioxide per gram of hydrocarbons in the feed gas stream.

* * * * *